United States Patent
Gorr et al.

(10) Patent No.: US 10,172,306 B2
(45) Date of Patent: Jan. 8, 2019

(54) PRODUCTION OF INGENOL, INGENOL ESTERS AND/OR TIGLIAN-3-ONE DERIVATIVES BY EUPHORBIACEAE PLANT CELL SUSPENSION CULTURES

(71) Applicant: Phyton Holdings, LLC, Fort Worth, TX (US)

(72) Inventors: Gilbert Gorr, Freiburg (DE); David Alexander Ullisch, Hamburg (DE); Yantree Devi Sankar-Thomas, Tornesch (DE); Thomas Selge, Escheburg (DE); Thomas Leibold, Delingsdorf (DE); Harald Heckenmüller, Hamburg (DE)

(73) Assignee: Phyton Holdings, LLC, Fort Worth, TX (US)

( * ) Notice: Subject to any disclaimer, the term of this patent is extended or adjusted under 35 U.S.C. 154(b) by 0 days.

(21) Appl. No.: 15/559,565

(22) PCT Filed: Mar. 18, 2016

(86) PCT No.: PCT/EP2016/055989
§ 371 (c)(1),
(2) Date: Sep. 19, 2017

(87) PCT Pub. No.: WO2016/150860
PCT Pub. Date: Sep. 29, 2016

(65) Prior Publication Data
US 2018/0042194 A1  Feb. 15, 2018

(30) Foreign Application Priority Data

Mar. 20, 2015  (EP) ..................... 15160160
Feb. 23, 2016  (EP) ..................... 16156907

(51) Int. Cl.
| | | |
|---|---|---|
| A61K 36/00 | (2006.01) |
| A01H 4/00 | (2006.01) |
| A61K 36/47 | (2006.01) |
| C12N 5/00 | (2006.01) |
| C12N 5/04 | (2006.01) |

(52) U.S. Cl.
CPC ............. A01H 4/001 (2013.01); A61K 36/47 (2013.01); C12N 5/0025 (2013.01); C12N 5/04 (2013.01)

(58) Field of Classification Search
CPC ...................................... A61K 36/00
See application file for complete search history.

(56) References Cited

FOREIGN PATENT DOCUMENTS

CN        102126941 A    7/2011
WO    WO 2005/079355 A2    9/2005

OTHER PUBLICATIONS

Adolf et al., Macrocyclic lathyrane type diterpene esters (jolkinols) from callus cultures and roots of Euphorbia lathyris. Planta Med. Jun. 1984;50(3):259-61.
WPI Database week 201204. AN 2011-K3852. Dec. 20, 2010.
Béres et al. Quantitative Analysis of Ingenol in Euphorbia species via Validated Isotope Dilution Ultra-high Performance Liquid Chromatography Tandem Mass Spectrometry. Phytochem Anal. Jan. 2018;29(1):23-29. doi: 10.1002/pca.2711. Epub Aug. 7, 2017.
Chagvardieff et al., Fatty acid patterns of neutral lipids from seeds, leaves and cell suspension cultures of Euphorbia characias. Phytochemistry. Jul. 1992;31(1):2351-2353.

*Primary Examiner* — Qiuwen Mi
(74) *Attorney, Agent, or Firm* — Wolf, Greenfield & Sacks, P.C.

(57) ABSTRACT

The present invention relates to a method of producing Ingenol, Ingenol esters and/or Tiglian-3-one derivatives, the method comprising the steps of: (a) culturing plant cells obtained from a plant selected from the family Euphorbiaceae in a nutrient medium in a suspension cell culture, wherein the cells produce Ingenol, one or more Ingenol esters and/or one or more Tiglian-3-one derivatives; and (b) recovering the Ingenol, the one or more Ingenol esters and/or the one or more Tiglian-3-one derivatives produced in (a). The present invention further relates to a plant suspension cell culture, wherein the cells are obtained from a plant selected from the family Euphorbiaceae, and wherein the plant cells produce Ingenol and/or one or more Ingenol ester and/or one or more Tiglian-3-one derivatives.

12 Claims, 6 Drawing Sheets

Figure 1:
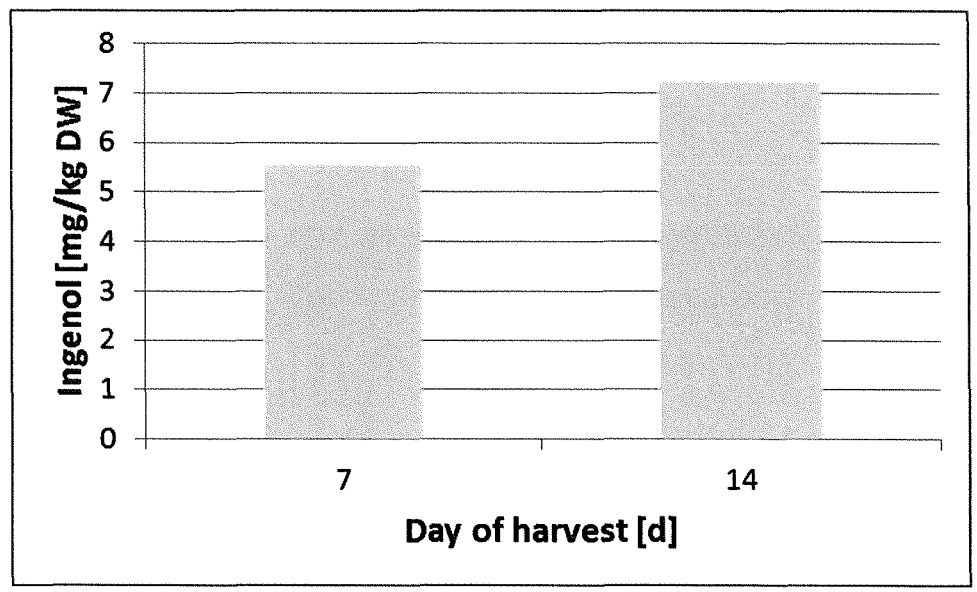

PRODUCTION OF INGENOL, INGENOL ESTERS AND/OR TIGLIAN-3-ONE DERIVATIVES BY EUPHORBIACEAE PLANT CELL SUSPENSION CULTURES

RELATED APPLICATIONS

This application is a national stage application under U.S.C. § 371 of PCT International Application No. PCT/EP2016/055989, filed Mar. 18, 2016, which claims foreign priority benefits under 35 U.S.C. § 119(a)-(d) or 35 U.S.C. § 365(b) of European application number 15160160.6, filed Mar. 20, 2015 and European application number 16156907.4, filed Feb. 23, 2016, the contents of each of which are incorporated herein by reference in their entireties.

The present invention relates to a method of producing Ingenol, Ingenol esters and/or Tiglian-3-one derivatives, the method comprising the steps of: (a) culturing plant cells obtained from a plant selected from the family Euphorbiaceae in a nutrient medium in a suspension cell culture, wherein the cells produce Ingenol, one or more Ingenol esters and/or one or more Tiglian-3-one derivatives; and (b) recovering the Ingenol, the one or more Ingenol esters and/or the one or more Tiglian-3-one derivatives produced in (a). The present invention further relates to a plant suspension cell culture, wherein the cells are obtained from a plant selected from the family Euphorbiaceae, and wherein the plant cells produce Ingenol and/or one or more Ingenol ester and/or one or more Tiglian-3-one derivatives. The present invention further relates to a plant cell biomass comprising plant cells obtained from the suspension cell culture of the invention, and comprising Ingenol and/or one or more Ingenol esters and/or one or more Tiglian-3-one derivatives. Also, the present invention relates to cryopreserved cells of the plant suspension cell culture of the invention as well as to a method of producing Ingenol, Ingenol esters and/or Tiglian-3-one derivatives based on these cryopreserved cells.

In this specification, a number of documents including patent applications and manufacturer's manuals is cited. The disclosure of these documents, while not considered relevant for the patentability of this invention, is herewith incorporated by reference in its entirety. More specifically, all referenced documents are incorporated by reference to the same extent as if each individual document was specifically and individually indicated to be incorporated by reference.

Plants contain a wide range of chemical compounds, including primary and secondary metabolites. In many cases, such secondary metabolites have been investigated for a pharmaceutical activity. The most prominent example is the anti-cancer compound paclitaxel, which is expressed by members of the genus *Taxus* and which has been shown to efficiently kill highly proliferating human cells, i.e. cells that show the fast cell growth that is characteristic for many tumours. For many years, products have been marketed which contain paclitaxel as the active pharmaceutical ingredient.

Another group of compounds that have been investigated for their activity on mammalian cell lines including numerous cancer cell lines are the naturally occurring compounds Ingenol, Ingenol esters and Tiglian-3-one derivatives. Although their activity on mammalian cells—including human cells—in vitro and in vivo is likely not based on a single mode of action, one important activity shared by the most prominent chemical members of this group of compounds is the regulation, in particular the activation, of protein kinase C. The interest in Ingenol, Ingenol esters and Tiglian-3-one derivatives has increased in recent years due to their important biological activities, mainly their anti-carcinogenic or anti-viral activities.

Whereas Ingenol is mainly used as a precursor to obtain biologically active Ingenol derivatives used in clinical praxis by means of different chemical methods, the Ingenol ester Ingenol-3-angelate as well as Tiglian-3-one 12-tigloyl-13-(2-methylbutanoyl)-6,7-epoxy-4,5,9,12,13,20-hexahydroxy-1-tigliaen-3-one provide significant biological activity. Ingenol-3-angelate is the most prominent compound approved for therapeutic use, i.e. for treatment of actinic keratosis (Leo Pharma: Picato®). Furthermore, Ingenol-3-angelate is considered as potentially active with respect to the treatment of solid tumours. 12-tigloyl-13-(2-methylbutanoyl)-6,7-epoxy-4,5,9,12,13,20-hexahydroxy-1-tigliaen-3-one has been described to be potentially suitable in the treatment of skin cancers including melanomas, squamous cell carcinomas (SCC) and basal cell carcinomas (BCC), head and neck cancers, breast cancers, prostate cancers and other tumours where injection can be guided by imaging.

At present, Ingenol, Ingenol esters and Tiglian-3-one derivatives are mainly sourced directly from the plant. The plants used as sources are members of the Euphorbiaceae family which is renowned in ethno-medicine [Mwine and van Damme 2011; Journal of Medicinal Plants Research: 5, 652-662]. Ingenol and Ingenol esters have, for example, been identified in many members of the genus *Euphorbia*, for example in seeds of the species *Euphorbia lathyris* and in the milky sap of the species *Euphorbia peplus*. Ingenol-3-angelate, for example, has been identified in *Euphorbia peplus, Euphorbia lathyris, Euphorbia antiquorum, Euphorbia helioscopia, Euphorbia paralias, Euphorbia drummondii, Euphorbia hirta* and *Euphorbia epithymoides*. Unfortunately, however, the amounts of Ingenol-3-angelate present in *Euphorbia peplus* are very low, with around 1.1 mg per kg plant material [Hohmann et al. 2000; Planta Medica: 66, 291-294].

To overcome supply issues of Ingenol-3-angelate, semi-synthetic approaches have recently been developed using Ingenol extracted from seeds of *Euphorbia lathyris* as the precursor [Liang et al. 2012; Synlett: 23, 2647-2652 and WO2013/050365]. Moreover, Jorgensen et al. 2013 described a 14-step synthetic chemical process of preparing Ingenol-3-angelate [Jorgensen et al. 2013; Science: 341, 878-882]. Although successful, both of these approaches have limitations: the yield for total synthesis of Ingenol-3-angelate is lower than 1% and the yield of Ingenol-3-angelate processed semi-synthetically from Ingenol isolated from 1 kg of *Euphorbia lathyris* seed powder is only up to 190 mg.

Tiglian-3-one derivatives have also been identified in members of the Euphorbiaceae family and are currently obtained by isolation from plants or plant parts of the genus *Fontainea* or *Hylandia*. Isolation of Tiglian-3-one derivatives from seeds, bark or flowers of the plant species *Fontainea picrosperma, Fontainea venosa* or *Hylandia dockrillii* is most commonly employed. 12-Tigloyl-13-(2-methylbutanoyl)-6,7-epoxy-4,5,9,12,13,20-hexahydroxy-1-tigliaen-3-one (EBC-46, formerly also referred to as EBI-46; also referred to as 12-tigloyl-13-(2-methylbutanoyl)-6,7-epoxy-4,5,9,12,13,20-hexahydroxy-1-tigliaen-3-one in the literature), for example, has been isolated from seeds of the Euphorbiaceae species *Fontainea picrosperma*. Extraction from plant material and purification of this compound yields only about 0.1% (1 g/kg plant material). Even more importantly, species expressing 12-tigloyl-13-(2-methylbutanoyl)-

6,7-epoxy-4,5,9,12,13,20-hexahydroxy-1-tigliaen-3-one only grow in Australia at a limited number of rainforest locations, thus limiting potential supply of this biologically active compound. Notably, chemical synthesis of 12-tigloyl-13-(2-methylbutanoyl)-6,7-epoxy-4,5,9,12,13,20-hexahydroxy-1-tigliaen-3-one has not been reported so far.

One approach to overcome the above described supply limitations could be the provision of in vitro cultures, for the re-production of the valuable plant-derived materials and, consequently, the secondary metabolites produced by said plant materials. In particular in vitro suspension cell cultures are, due to their easy scalability, promising alternatives to supply Ingenol, Ingenol esters and/or Tiglian-3-one derivatives at high quantities in a sustainable manner and independent from the natural environment.

In vitro cultures, including suspension cultures, have been reported for a variety of members of the Euphorbiaceae family. For example, callus cultures of *Euphorbia peplus* have been described by Aljibouri et al. [Aljibouri et al. 2014; Journal of Biotechnology Research Center (Special Edition): 8, 66-71; Aljibouri et al. 2015; ISBN: 978-3-659-75695-5] as well as Tideman and Hawker [Tideman and Hawker 1982; Annals of Botany: 49, 273-279]. However, de novo expression of Ingenol, Ingenol esters and/or Tiglian-3-one derivatives in these cultures in vitro—either in callus cultures or in suspension cultures—has not been shown by any of these groups. For example, Yamamoto [Yamamoto; 1991; Biotechnology in Agriculture and Forestry: 15, 247-257; In: Medicinal and Aromatic Plants III (ed. by Y. P. S. Bajaj); Springer-Verlag Berlin Heidelberg] investigated *Euphorbia* spp and described in much detail the expression and production of anthocyanin in *Euphorbia millii*. However, the only other secondary metabolites that were found to be produced in *Euphorbia* cell cultures were fatty acids, phytosterols, triterpenes and anthocyanins, but not Ingenol, Ingenol esters and/or Tiglian-3-one derivatives. Even more, Adolf et al. [Adolf et al. 1984; Planta Medica: 50, 259-261] describe callus cultures obtained from *Euphorbia lathyris* and show the expression of diterpene esters of the lathyrane type in these callus cultures. However, although the presence of diterpene esters of the ingenane type in the starting materials was shown, they were no longer present in the final callus cultures, thus suggesting that the expression of Ingenol and Ingenol esters is lost under in vitro culture conditions. Thus, no cell culture system of plant species of the Euphorbiaceae family has been successfully established yet that expresses Ingenol, Ingenol esters and/or Tiglian-3-one derivatives in vitro.

Accordingly, despite the fact that a lot of effort has been invested into methods that enable the economic and simple production of Ingenol, Ingenol esters and/or Tiglian-3-one derivatives, there is still a need for improved approaches suitable for large scale production. Moreover, although there is a huge demand in particular for Ingenol-3-angelate, as underlined by the efforts to develop semi-synthetic and synthetic production methods, plant cell cultures to specifically produce Ingenol, Ingenol esters and/or Tiglian-3-one derivatives have not been envisaged in the literature at all. Even more, in those instances where plant cell cultures were analysed for the expression of secondary metabolites, no expression of ingenanes—including Ingenol and/or Ingenol esters—has been detected or described.

This need is addressed by the provision of the embodiments characterised in the claims.

Accordingly, the present invention relates to a method of producing Ingenol, Ingenol esters and/or Tiglian-3-one derivatives, the method comprising the steps of: (a) culturing plant cells obtained from a plant selected from the family Euphorbiaceae in a nutrient medium in a suspension cell culture, wherein the cells produce Ingenol, one or more Ingenol esters and/or one or more Tiglian-3-one derivatives; and (b) recovering the Ingenol, the one or more Ingenol esters and/or the one or more Tiglian-3-one derivatives produced in (a).

Ingenol and Ingenol esters, in accordance with the present invention, are chemical compounds possessing an ingenane backbone.

Ingenol ((1aR, 2S, 5R, 5aR, 6S, 8aS, 9R, 10aR)-1a, 2, 5, 5a, 6, 9, 10, 10a-octahydro-5, 5a, 6-trihydroxy-4-(hydroxymethyl)-1, 1, 7, 9-tetramethyl-1H-2, 8a-methanocyclopenta[a]cyclopropa[e]cyclodecen-11-one; CAS-No.: 30220-46-3) is well known in the art. It structurally relates to the ingenanes and is shown below in Formula I:

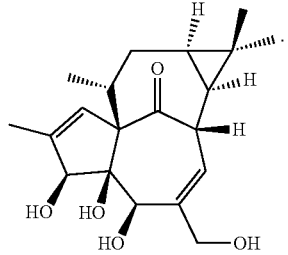

Formula I

The term "Ingenol esters", as used herein, also structurally relates to ingenanes. Preferably, the Ingenol esters are selected from the group consisting of ingenol-3-angelate, 20-deoxy-ingenol-3-angelate and 20-O-acetyl-ingenol-3-angelate.

A particularly preferred Ingenol ester in accordance with the present invention is Ingenol-3-angelate (CAS-No.: 75567-37-2), also known under the name ingenol mebutate or 2-Methyl-2(Z)-butenoic acid (1aR,2S,5R,5aS,6S,8aS,9R,10aR)-5, 5a-dihydroxy-4-(hydroxymethyl)-1, 1, 7, 9-tetramethyl-11-oxo-1a, 2, 5, 5a, 6, 9, 10, 10a-octahydro-1H-2,8a-methanocyclopenta-[a]cyclopropa[e]cyclodecen-6-yl ester. Ingenol-3-angelate is shown below in Formula II:

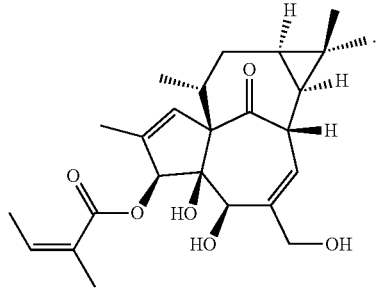

Formula II

The term "Tiglian-3-one derivatives" (Tiglian-3-one is alternatively named in the art "Tigliaen-3-one" or "Tiglien-3-one"), as used herein, relates to all saturated, mono- or oligo-unsaturated, deoxy- and additionally hydroxylated tetracyclic diterpenes, and corresponding esters, containing the Tiglianebackbone, a keto-functionality in position 3 of the Tigliane moiety and an epoxide element in the 6,7-position of the Tigliane backbone. Preferably, the Tiglian-3-one derivative is selected from the group consisting of 12-tigloyl-13-(2-methylbutanoyl)-6,7-epoxy-4,5,9,12,13,20-hexahydroxy-1-tigliaen-3-one (EBC-46 or EBI-46); 12, 13-di-(2-methylbtanoyl)-6, 7-epoxy-4,5,9,12,13,20-hexahydroxy-tigliaen-3-one (EBI-47); 12-(dodeca-2,4,6-trienoyl)-13-(2-methylbutanoyl)-6,7-epoxy-4,5,9,12,13,20-hexahydroxy-1-tigliaen-3-one (EBI-59); 12-(deca-2,4-dienoyl)-6,7-epoxy-4,5,9,12,13,20-hexahydroxy-1-tigliaen-3-one (EBI-61); 12,13-di-(2-methylbutanoyl)-1,2-2H-1,2,6,7-diepoxy-6-carboxy-4,5,9,12,13-pentahydroxy-tigliaen-3-one and 12,13-di-(2-methylbutanoyl)-5,20-di-acetyoyl-4,5,9,12,13,20-hexahydroxy-tigliaen-3-one; all of which are described in e.g. WO07070985.

One particularly preferred Tiglian-3-one derivative in accordance with the present invention is 12-tigloyl-13-(2-methylbutanoyl)-6,7-epoxy-4,5,9,12,13,20-hexahydroxy-1-tigliaen-3-one EBC-46), which is shown in Formula III below:

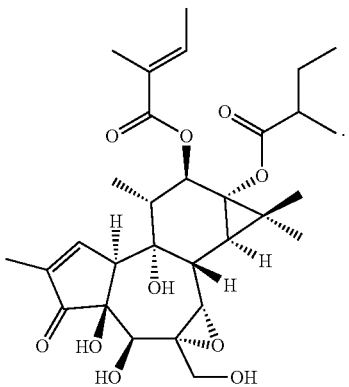

Formula III

The method of the present invention comprises steps (a) and (b) described in the following. The term "comprising", as used herein, denotes that further steps and/or components can be included in addition to the specifically recited steps and/or components. However, this term also encompasses that the claimed subject-matter consists of exactly the recited steps and/or components.

Step (a) of the method of the present invention encompasses that plant cells are cultured in a nutrient medium in a suspension cell culture.

The plant cells, in accordance with the present invention, are cells obtained from a plant selected from the family Euphorbiaceae. Plants of the family Euphorbiaceae include, without being limiting plants of the genus *Elaeophorbia, Euphorbia, Fontainea, Hylandia*. Non-limiting examples of species of these genera are provided in Table 1 below.

TABLE 1

Exemplary genera and species of the Euphorbiaceae family

| Genus | Exemplary Species |
|---|---|
| Elaeophorbia | Elaeophorbia drupifera |
| Elaeophorbia | Elaeophorbia grandiflora |
| Euphorbia | Euphorbia acrurensis |
| Euphorbia | Euphorbia antiquorum |
| Euphorbia | Euphorbia biglandulosa |
| Euphorbia | Euphorbia canariensis |
| Euphorbia | Euphorbia cooperi |
| Euphorbia | Euphorbia cornigera |
| Euphorbia | Euphorbia cofinifolia |
| Euphorbia | Euphorbia deightonii |

TABLE 1-continued

Exemplary genera and species of the Euphorbiaceae family

| Genus | Exemplary Species |
|---|---|
| Euphorbia | Euphorbia desmondi |
| Euphorbia | Euphorbia drupifera |
| Euphorbia | Euphorbia ebracteolata |
| Euphorbia | Euphorbia esula |
| Euphorbia | Euphorbia fischeriana |
| Euphorbia | Euphorbia grandiflora |
| Euphorbia | Euphorbia helioscopia |
| Euphorbia | Euphorbia hermentiana |
| Euphorbia | Euphorbia iberica |
| Euphorbia | Euphorbia ingens |
| Euphorbia | Euphorbia jolkini |
| Euphorbia | Euphorbia kamerunica |
| Euphorbia | Euphorbia kansui |
| Euphorbia | Euphorbia lathyris |
| Euphorbia | Euphorbia leuconeura |
| Euphorbia | Euphorbia matabelensis |
| Euphorbia | Euphorbia megalantha |
| Euphorbia | Euphorbia millii |
| Euphorbia | Euphorbia myrsinites |
| Euphorbia | Euphorbia nematocypha |
| Euphorbia | Euphorbia nubica |
| Euphorbia | Euphorbia palustris |
| Euphorbia | Euphorbia paralias |
| Euphorbia | Euphorbia peplus |
| Euphorbia | Euphorbia petiolata |
| Euphorbia | Euphorbia pilosa |
| Euphorbia | Euphorbia quadrialata |
| Euphorbia | Euphorbia quinquecostata |
| Euphorbia | Euphorbia resinifera |
| Euphorbia | Euphorbia royleana |
| Euphorbia | Euphorbia segueiriana |
| Euphorbia | Euphorbia serrata |
| Euphorbia | Euphorbia sieboldiana |
| Euphorbia | Euphorbia tirucalli |
| Euphorbia | Euphorbia triangularis |
| Euphorbia | Euphorbia trigona |
| Euphorbia | Euphorbia virgata |
| Euphorbia | Euphorbia epithymoides |
| Fontainea | Fontainea australis |
| Fontainea | Fontainea borealis |
| Fontainea | Fontainea fugax |
| Fontainea | Fontainea oraria |
| Fontainea | Fontainea pancheri |
| Fontainea | Fontainea picrosperma |
| Fontainea | Fontainea rostrata |
| Fontainea | Fontainea subpapuana |
| Fontainea | Fontainea venosa |
| Hylandia | Hylandia dockrillii |

In accordance with the present invention, the plant cells can be from one single plant, or, alternatively, from more than one plant. In the latter case, the cells can be obtained from several plants of the same strain, or from several plants of the same variety, from several plants of the same subspecies, from several plants of the same species, or from several plants of the same genus. The cells may also be obtained from several different plants that all belong to the family Euphorbiaceae. Preferably, however, the cells are from one species, more preferably from one sub-species, even more preferably from one variety and most preferably from one strain.

The plant tissue used to initiate the cell culture can be any plant tissue. Non-limiting examples of tissue to obtain cells for culture include plant parts such as e.g. roots, leaves, stems, meristems and seeds. Preferably, the starting material is selected from roots, leaves and stems. More preferably, the starting material is selected from roots, leaves and stems of young in vitro cultivated seedlings. Means and methods for detecting the production of Ingenol, Ingenol esters and/or Tiglian-3-one derivatives in the respective material are well known in the art and are discussed in more detail herein below.

The cells obtained from these parts can be any kind of cells, such as e.g. undifferentiated cells, de-differentiated cells, meristematic cells, embryogenic cells, non-embryonic cells or mixtures thereof. Cells for culture can also be obtained via the intermediate step of forming a callus from such plant parts, preferably a friable callus, as discussed in more detail herein below. The plant cells can be obtained directly from a plant or a callus or can be cryopreserved cells that were obtained from a plant or a callus or a suspension culture at an earlier time.

In accordance with the present invention, a buffered or non-buffered aqueous nutrient medium is employed. The term "nutrient medium", as used herein, refers to a medium that is suitable for the cultivation of plant cell suspension cultures. Nutrient media are well established in the art and can be based, for example, on Murashige and Skoog Basal Salts (MS), Schenk and Hildebrandt Basal Salts (SH) or a compound composition according to Gamborg (B5).

The term "nutrient medium" encompasses both "growth medium" and "production medium". The term "growth medium", as used herein, refers to a nutrient medium that favours the growth of cultured cells. In a preferred embodiment, the growth medium provides a growth increase of at least 50% in one week. The growth increase can be determined based on e.g. dry or fresh weight. Preferably, the growth increase is determined based on fresh weight. A "production medium", in accordance with the present invention, is a nutrient medium that favours the production of Ingenol, Ingenol esters and/or Tiglian-3-one derivatives. It will be appreciated that a certain amount of growth can also occur in a production medium and that a certain amount of production can take place in a growth medium. However, in accordance with the present invention, growth is favoured over production in the growth medium employed while production is favoured over growth in the production medium employed. In accordance with the present invention, the method of the invention can include one or more steps of culturing the cells in a growth medium and/or one or more steps of culturing the cells in a production medium.

Exemplary production media—include, but are not limited to, media comprising a salt base (e.g., MS or SH), plus optionally macronutrients, micronutrients, vitamins, plant growth regulators, amino acids, elicitors and/or a carbon source, preferably sucrose. The production medium may also comprise sources of inorganic or organic nitrogen. Preferred amounts of sucrose to be employed are between 0.01% (w/v) and 10% (w/v), more preferably between 0.05 and 6% (w/v), such as e.g. between 0.25% (w/v) and 4% (w/v). Sucrose may be obtained from e.g. Sigma Aldrich, Carl Roth and/or VWR. Preferred amounts of nitrogen to be employed are between 0.05% (w/v) and 10% (w/v), more preferably between 0.1% (w/v) and 5% (w/v) such as e.g. between 0.25% (w/v) and 2% (w/v). Nitrogen may be obtained from nitrate, ammonium and amino acids, or a mixture thereof. Nitrogen sources may be obtained from e.g. Sigma Aldrich, Carl Roth and/or VWR.

The essential nutrients in plant cell or tissue culture media include macronutrients and micronutrients. For satisfactory growth and morphogenesis macronutrients such as nitrogen (N), phosphorus (P), potassium (K), calcium (Ca), magnesium (Mg) and sulphur (S) are consumed by plant cells and tissue in larger quantities. Typical content of macronutrients in plant tissue is about 0.2% to about 4% on a dry matter weight basis. In contrast, micronutrients are consumed at low quantities and are typically present below 0.02% (on dry matter weight basis) in plant tissue. Micronutrients include iron (Fe), manganese (Mn), zinc (Zn), boron (B), copper (Cu), molybdenum (Mo), chlorine (Cl) as well other micronutrients well known in the art.

Vitamins include any natural or synthetic vitamin utilized by the cells such as thiamine, nicotinic acid and pyridoxine. These can be used singly or in any combination. Vitamins can preferably be used at concentrations between 10 µg/l and 100 mg/l, more preferably between 50 µg/l and 10 mg/l and most preferably at about 0.5 mg/l for nicotinic acid or pyridoxine hydrochloride and 0.1 mg/l for thiamine hydrochloride.

It is well known in the art that the production of secondary metabolites in plant suspension cultures is influenced by plant growth regulators. Plant growth regulators include a wide variety of substances known in the art including, without being limiting, auxin and/or cytokinin/cytokinin-like compounds, e.g., indolebutyric acid (IBA), naphthalene acetic acid (NAA), picloram, dicamba, benzylaminopurine (BAP), kinetin, zeatin, thidiazuron, 2,4-dichlorophenoxy-acetic acid (2,4-D) and indole acetic acid (IAA). By e.g. changing the relation of auxin to cytokinin/cytokinin-like compounds in the nutrient medium, the production of Ingenol, Ingenol esters and/or Tiglian-3-one derivatives can be enhanced. The effect of individual plant growth regulators on the production of Ingenol, Ingenol esters and/or Tiglian-3-one derivatives in a particular cell suspension culture in accordance with the present invention can be experimentally confirmed without further ado. For example, the amount of Ingenol, Ingenol esters and/or Tiglian-3-one derivatives produced in the presence and absence, or in the presence of two or more different concentrations, of a particular plant growth regulator can be determined to obtain information on a potential influence of this plant growth regulator on the production rate of these compounds under these particular cell culture conditions. Preferred amounts of plant growth regulators include concentrations of about 0.001 µmol/l to about 2 mmol/l, preferably about 0.01 µmol/l to about 1 mmol/l.

Amino acids include any natural or synthetic amino acid utilized by the cells such as glutamine, glutamic acid, and aspartic acid. These can be used singly or in any combination. Amino acids can preferably be used at concentrations between 10 mg/l and 10 g/l, more preferably between 50 mg/l and 5 g/l.

Elicitors include, but are not limited to, jasmonic acid, methyl jasmonate, natural or synthetic jasmonates, tuberonic acid, cucurbic acid, coronatine, indanoyl amides such as 6-ethyl-indanoyl isoleucine, alkanoic acids, 12-oxo-phytodienoic acid, salicylic acid, systemin, volicitin, and compounds related to any of these exemplary elicitors. Elicitors further include, without being limiting, oligosaccharides, e.g., oligosaccharides from plants, fungi, or microbes; chitosan; chitin; glucans; cyclic polysaccharides; preparations containing cellular material from bacteria, fungi, yeasts, plants, or insects; material contained in insect saliva or secretions; inhibitors of ethylene biosynthesis or action in plants, especially silver-containing compounds or complexes, cobalt, and aminoethoxyvinylglycine. Elicitors especially useful for the production of the Ingenol, Ingenol esters and/or Tiglian-3-one derivatives include jasmonic acid-related compounds such as jasmonates, salicylic acid is also useful elicitor. In accordance with the present invention, heavy metals such as cadmium, vanadium and silver are also useful in salt or complex form. Chitin, chitosans (especially chitosan glutamate), N-acetyl oligosaccharides, pectic polysaccharides, fungal glycans (containing 5 or more sugars), fungal glycoproteogalactans, sphingolipid elicitors, pectic polysaccharides, and arachidonic acid are also useful elicitors in accordance with the present invention. Typical quantities of elicitors for cell culture are known in the art. For example, preferred amounts of methyl jasmonate are between 0.1 to 3 µM, most preferably 1 µM as shown in Example 11. To give another example, preferred amounts of salicylic acid are between 1 to 200 µM, most preferably 30 µM as shown in Example 10.

A particularly preferred production medium comprises a salt base (e.g., MS or SH or B5), plus 0.25% sucrose.

Exemplary growth media include, but are not limited to, media comprising a salt base (e.g., MS or SH or B5), plus a carbon source, preferably sucrose and optionally macronutrients, micronutrients, vitamins, plant growth regulators and/or amino acids. Preferred amounts of sucrose to be employed are between 0.01% (w/v) and 6% (w/v), more preferably between 0.1% (w/v) and 5% (w/v), such as e.g. between 1% (w/v) and 3% (w/v) and most preferably the amount is about 2% (w/v). Preferred amounts of nitrogen to be employed are between 0.01% (w/v) and 10% (w/v), more preferably between 0.05% (w/v) and 5% (w/v) such as e.g. between 0.2% (w/v) and 1% (w/v) and most preferably about 0.28% (w/v). Nitrogen may be obtained from nitrate, ammonium or amino acids, or a mixture thereof. Preferred amounts of macronutrients, micronutrients vitamins, plant growth regulators and amino acids are as detailed above. Growth medium does not contain elicitors.

A particularly preferred growth medium comprises a salt base (e.g., MS or SH or B5), plus 2% sucrose.

An even more preferred growth medium comprises a salt bases (e.g., MS or SH or B5), plus 2% sucrose and a combination of 2.3 µmol/L 2,4-dichlorophenoxyacetic acid and 2.2 µmol/l benzylaminopurine.

A further preferred growth medium comprises a salt base (e.g., MS or SH or B5), plus 2% sucrose, a combination of 2.3 µmol/L 2,4-dichlorphenoxyacetic acid and 2.2 µmol/l benzylaminopurine and a combination of 0.1 mg/l thiamine hydrochloride, 0.5 mg/l nicotinic acid and 0.5 mg/l pyridoxine hydrochloride.

The nutrient medium is typically prepared to contain all of the desired ingredients before the cells are placed into the nutrient medium. In addition, further compounds or supplementary ingredients can also subsequently be introduced into the culture after the cells and medium are first contacted. For example, these ingredients, such as additional carbohydrate, can be supplied in a feed stream intermittently or continuously as needed.

It is also desirable to reduce or avoid oxidative browning in the cell culture as this negatively influences the quality of the cell culture and subsequent recovery. To this end, so-called "anti-browning agents" can be added to the nutrient medium to prevent the formation of pigments during cell cultivation. These pigments include phenolics and related compounds that are generally observed to have a deleterious effect on cell growth, viability, and product formation. A typical, non-limiting example of an anti-browning agent used in the nutrient media according to this invention is ascorbic acid. Anti-browning agents are typically incorporated into the medium at a concentration range of 10 ppb to 1000 ppm. Alternatively, or additionally, non-embryogenic cells can be employed, as these are less susceptible to browning than embryonic cells. In accordance with the present invention, the term "non-embryogenic cells" refers to undifferentiated, dedifferentiated and meristematic cells. The non-embryogenic cells can be distinguished from embryogenic cells by the presence of (a) vacuole(s), whereas embryogenic cells are highly cytoplasmic and non-vacuolated. Means and methods to obtain non-embryogenic cells for use in the method of the invention are well known in the art. Non-limiting examples for obtaining non-embryogenic cells include their derivation from a friable callus. To provide an example, an inoculum from such a friable callus of about 0.01 to about 10 g/25 ml can be employed to prepare non-embryogenic suspension cultures for use in the method in accordance with the present invention.

It will be appreciated that the rate of production of Ingenol, Ingenol esters and/or Tiglian-3-one derivatives is not determined by a single rate-limiting step, but by a complex interaction between a plurality of limiting factors. Relief of any one of the limiting factors will enhance production of Ingenol, Ingenol esters and/or Tiglian-3-one derivatives, although the magnitude of this enhancement will depend on the particular culture conditions, which determine the relative limiting effects of other steps in the production of Ingenol, Ingenol esters and/or Tiglian-3-one derivatives. Such culture conditions that affect the interaction between various limiting factors include the genetic make-up of the cells, the composition of the culture medium, and the temperature employed in the culture.

General cell culture conditions are well known in the art. The levels of gases such as oxygen, carbon dioxide, and ethylene can be controlled to favour the production of Ingenol, Ingenol esters and/or Tiglian-3-one derivatives or to favour biomass accumulation. Routine cultivation in lab scale cultivation vessels held in an atmosphere of air, with typical closures such as sheets, plugs, or caps result in dissolved oxygen levels below air saturation and levels of carbon dioxide and ethylene higher than that present in atmospheric air. Thus, routinely, carbon dioxide levels in the head-space of the culture are typically greater than about 0.03% v/v. However, the concentrations of carbon dioxide and/or ethylene can be adjusted to either favour production of Ingenol, Ingenol esters and/or Tiglian-3-one derivatives or, alternatively, to favour cell propagation.

In one embodiment, production of Ingenol, Ingenol esters and/or Tiglian-3-one derivatives is favoured by adjusting the carbon dioxide level in the head-space or aeration stream to be about 0.1% (approximately 3-times atmospheric) to about 10%, preferably about 0.3% to about 7% in equilibrium with the liquid at the temperature of operation. In another embodiment, ethylene is less than about 500 ppm and preferably less than 200 ppm as measured in the gas phase in equilibrium with the liquid phase at the temperature of operation. Gases can also be provided independently, e.g., the sources of oxygen and carbon dioxide can be different.

Dissolved gases can be controlled by varying one or more of: the agitation rate, the composition of aeration gas, the supply rate of the aeration gas, the venting rate of the aeration gas, and the total pressure in the cultivation vessel. Agitation rates can be controlled at about 1 to about 500 per minute (rotations or oscillations of agitators or circulations of fluid). The supply rate of gas can be any rate that is appropriate for achieving a dissolved gas concentration that is adequate or optimal for cell biomass accumulation or maintenance or product formation. Preferably, this rate is about 0.01 to about 10 volumes of gas per volume of culture broth per minute and can be supplied directly into the culture liquid, or into a separate portion of liquid that is subsequently mixed with the rest of the culture, or into the head space of the culture, or into a device for contacting the gas species with the culture medium. In one embodiment, dissolved oxygen concentrations are controlled at about 10% to about 200%, preferably about 20% to about 150%, of air saturation at the operating temperature. Of course, it is possible that for various operational reasons, e.g., temporary reduction in aeration, the dissolved oxygen level could be as low as zero for periods of time ranging from a few minutes to several hours. Specific useful combinations of oxygen, carbon dioxide, and ethylene, outside these ranges may be discovered through routine experimentation and are considered to be within the scope of this invention.

Preferably, a temperature of about 10° C. to about 30° C. is adjusted, more preferably the temperature is adjusted to a value between about 15° C. to about 28° C., even more preferably to a value between about 23° C. to about 27° C., and most preferably it is adjusted to about 25° C.

It is also preferred that the cell culture conditions comprise conditions of shaking, preferably at about 50 rpm to about 300 rpm such as e.g. between about 80 rpm and about 200 rpm, preferably between about 100 rpm to about 150 rpm and most preferably the shaking frequency is about 130 rpm.

As regards to shake flask scale, most preferred are cell culture conditions comprising conditions of shaking at a shaking frequency of about 130 rpm, in darkness and at a temperature of about 23° C. to 27° C., preferably about 25° C.

The term "about", as used herein, encompasses the explicitly recited values as well as small deviations therefrom. In other words, a shaking speed of "about 130 rpm" includes, but does not have to be exactly the recited amount of 130 rpm but may differ by several rpm, thus including for example 131 rpm, 132 rpm, 129 rpm, or 128 rpm. The skilled person is aware that such values are relative values that do not require a complete accuracy as long as the values approximately correspond to the recited values. Accordingly, a deviation from the recited value of for example about 15%, more preferably of about 10%, and most preferably of about 5% is encompassed by the term "about". These deviations of about 15%, more preferably of about 10% and most preferably of about 5% hold true for all embodiments pertaining to this invention wherein the term "about" is used.

It is further preferred that the cell cultures are sub-cultured at regular intervals. For example, for maintenance of the cell culture it is preferred that the cultures are sub-cultured every 6 to 8 days. For harvesting biomass, on the other hand, the cultures are allowed to grow for about 12 to 16 days before harvest. It is also preferred that the cell culture is carried out under sterile conditions.

One objective of the invention is to obtain commercially significant amounts of the end product from aerated bioreactors. Another objective is to provide methods of increasing the volumetric yield.

Whereas scale-up of cultivation in bioreactors is performed by transfer of biomass from one bioreactor to another, initial transfer of biomass into bioreactor environment is performed by inoculation with viable biomass propagated in shake flasks. Initial inoculation of a bioreactor is performed under sterile conditions e.g. by use of sterilized inoculation flasks—capable to be connected under sterile conditions to the bioreactor—which are filled under sterile environment with viable Euphorbiaceae biomass previously cultivated under sterile conditions in shake flasks. Preferred concentrations of viable Euphorbiaceae biomass for inoculation range from about 5 g fresh weight/l to about 100 g fresh weight/l, even more preferred amounts of viable Euphorbiaceae biomass for inoculation range from about 10 g fresh weight/l to about 60 g fresh weight/, and most preferred amounts of viable Euphorbiaceae biomass for inoculation range from about 20 g fresh weight/l to about 40 g fresh weight/. To this end, different kinds of bioreactors can be used. The most common bioreactor for a wide range of plant cell suspensions is the reusable stainless steel stirred bioreactor. Single-use bioreactor systems can be used as an orbitally shaken systems e.g. Infors' Multitron with ShakerBag or OrbShake Bioreactor [Kuhner AG]. Single-use bioreactors in which the culture broth in the disposable cultivation bag is vertically oscillating by a wave-mixed motion can be used for propagation as well as for production. In all wave mixed bioreactors, a wave is induced as well as oxygen is bubble-free introduced into the culture broth by either rocking a bag (AppliFlex™, BIOSTAT® CultiBag RM, Wave Bioreactor™) or raising respectively lowering sections of a platform, where a bag is placed on.

In addition, general process operations in this field are also well known in the art and can be adjusted without further ado by the skilled person. These general process operations for a plant cell culture process relate to the way that nutrients, cells, and products are added or removed with respect to time [Payne, G., et al., 1991; "Plant Cell and Tissue Culture in Liquid System", (Hanser Publishers)].

Ingredients, such as e.g. carbohydrates, nutrients, vitamins, anti-oxidants and elicitors provided to the cells can be provided in a number of different ways. Ingredients can be added in a particular stage of growth such as lag, exponential, or stationary. All ingredients can be provided at once and then, after a suitable period of time, the resulting product can be recovered. In other circumstances, not all ingredients can be provided all at once. Rather, one or more of them may be provided at different times during the cultivation. Further, the additions can be discontinuous or staggered as to the time of initial contact and the duration of such provision can vary for different ingredients. Ingredients can be provided in a plurality of parts. One or more ingredients can be supplied as part of solutions separately contacted with the cell culture or portions thereof.

Portions of the suspension culture can be removed at any time or periodically and used for cryopreservation, further cell propagation, production, and/or recovery. Such cell-containing portions can be exposed further to nutrients or other ingredients as desired. Exemplary procedures of transfer of suspension cultures are described herein. Preferably, medium containing nutrients or other ingredients is added to replenish a portion or all of the removed volume. Portions of such removed material can be added back into the original culture, for instance, cells and medium can be removed, a portion of the cells or medium can be used for product recovery and the remaining cells or medium can be returned.

The supply rate of ingredients to the culture or levels of various ingredients in the culture can be controlled to advantageously produce and recover the product. Separate portions of the culture can be exposed to ingredients in any of the foregoing modes and then combined in proportions determined to be advantageous for production. Also the cell content of the culture can be adjusted to advantageously yield product or propagate cells. Adjustment of cell content can be advantageously combined with strategies for contacting with nutrients or other ingredients.

The replenishment of fresh medium to cells undergoing active biosynthesis may also be employed to enhance production by providing essential nutrients that have been depleted during the cultivation. Miyasaka et al. were able to stimulate stationary phase cells of *Salvia miltiorhiza* to produce the diterpene metabolites cryptotanshinone and ferruginol simply by adding sucrose to the medium [Miyasaka et al., "Regulation of Ferruginol and Cryptotanshinone Biosynthesis in Cell Suspension Cultures of *Salvia miltiorrhiza*," Phytochemistry 25: 637-640 (1986)]. It is thus preferred to employ a periodic-medium-exchange protocol for the cell culture method of the present invention, in order to provide similar benefits.

It is further contemplated that the amount of medium exchanged, the frequency of exchange, and the composition of the medium being replenished can be varied as required. The ability to stimulate biosynthesis by medium exchange has important implications for the design and operation of an efficient commercial process in the continuous, semi-continuous, or fed-batch mode. In a "fed-batch" operation, particular medium components such as nutrients are supplied either periodically or continuously. In a preferred embodiment, a substantial portion, such as e.g. a portion of about 70% to 90%, of the contents of a batch culture is replaced by fresh medium for continued cell growth and production; this process mode resembles a "repeated batch" operation and is termed a "semi-continuous process." In an alternative, preferred embodiment, the process is "continuous," that is, fresh medium is continuously supplied, and effluent medium is continuously or repetitively removed.

All concentrations stated herein refer to the average initial values in the extracellular medium after addition. Concentrations in feed solutions and, therefore, local concentrations in contact with the cells can be higher than those indicated. In those cases where preparations containing cellular material, such as e.g. inactivated mycel from e.g. *Fusarium* spec. such as *F. heterosporium, Gibberella zeae*, or *Pythium* spec. such as *P. graminicola* are to be added, the amounts to be added can be based on the concentration of a specific constituent of the preparation or the amount can represent a certain fraction of the culture volume. The desired effect, e.g., either growth or production, can be achieved by manipulating the media conditions described above by adding, removing, or changing the concentration of one or more nutrients or other agents. Starting from the concentrations indicated herein as a guide, routine optimisation can discern specific components, or combination of components, and concentrations, that are particularly useful to maximise Ingenol, Ingenol esters and/or Tiglian-3-one derivative production. In addition to modifying the medium components, other reaction conditions can also be modified to obtain the desired result, for example by manipulating conditions including, but not limited to, temperature and pH or by manipulating any combination of these conditions. Media conditions can readily be modified, and manipulated in view of the guidance provided herein and available from the art to achieve optimum performance, which may vary between cell lines.

The term "suspension culture", as used herein, refers to the culture of cells dispersed in a liquid medium. In a preferred embodiment, the suspension culture is a culture of non-embryogenic cells dispersed in a liquid nutrient medium. It is readily understood that suspension cultures comprise cells in various stages of aggregation. A range of aggregate sizes are encountered in the suspensions with sizes ranging from tens of microns in diameter (single cells or few-aggregated cells) to aggregates many millimeters in diameter, consisting of many thousands of cells. Suspension cultures comprising such aggregates are encompassed by the method of the present invention.

To transfer cells into a suspension culture, they are for example removed from a callus and transferred to sterile culture vessels containing nutrient medium. Suspension culture can, for example, be initiated using a nutrient medium that was successful in the previous generation of e.g. a friable callus culture, preferably without gelling agents. However, it is appreciated that optimised media for suspension culture may differ from the optimum for callus of the same cell line. Alternatively, or additionally, the plant cell culture may also be derived from a cryopreserved collection of cells.

Once initiated, a suspension culture can be further cultivated, either by (i) separating the cells substantially from the medium (typically by filtration, e.g. vacuum filtration) and then reintroducing a portion to a medium containing nutrients, or by (ii) transferring a volume of culture broth (cells and medium) into a medium containing nutrients, or by (iii) allowing the cells to settle followed by removal of any portion of medium already present and reintroducing nutrient-containing medium. When cells and media are transferred volumetrically, the ratio of the transferred volume to the final volume can be preferably from about 1% to substantially all of the volume, more preferably from about 5% to about 50% and even more preferably from 10% to about 20%. In case all of the volume is transferred, fresh nutrients can be supplied in a concentrated form, resulting in only a small volume increase. The culture can thus be divided into portions, which can individually be further employed to either grow cells further, to produce Ingenol, Ingenol esters and/or Tiglian-3-one derivatives or both. Each portion can, but need not, be cultured under the same conditions or as the original culture. The duration of growth can be extended by supplementing a partially depleted medium with nutrients.

The cells grown in accordance with the method of the present invention produce Ingenol, one or more Ingenol esters and/or one or more Tiglian-3-one derivatives, as defined above. Preferably, the cells produce one or more of these bioactive compounds in a detectable amount under the cell culture conditions shown in the appended examples.

The term "one or more" as used herein, for example in the term "one or more Ingenol esters" or "one or more Tiglian-3-one derivatives" refers to exactly one but also to more than one, such as e.g. two, three, four, five, six, seven and so on. Moreover, the term "one or more" does not define the actual number of one type of molecule present, but refers to the number of distinct molecules of the recited class. For example, the term "one or more Ingenol esters" refers to exactly one Ingenol ester such as e.g. the preferred Ingenol-3-angelate, but also to more than one, such as e.g. two, three, four, five, six, seven etc. different Ingenol esters. The same applies mutatis mutandis to the term "one or more Tiglian-3-one derivatives".

In the second step of the method of the present invention, the Ingenol, Ingenol esters and/or Tiglian-3-one derivatives that has/have been produced by the cultured cells is/are recovered. The Ingenol, Ingenol esters and/or Tiglian-3-one derivatives can be recovered from the entire culture or from any portion of culture, and they can be recovered at any time during the cultivation or after the completion of the culture period. Preferably, the cells are cultured for about 12 to 16 days before recovery, more preferably the cells are cultured for about 12 to 16 days without any intermediate step of sub-cultivation. It will be appreciated that all of the bioactive compounds of the group consisting of Ingenol, Ingenol esters and/or Tiglian-3-one derivatives produced can be recovered, or, preferably, that one or more particular bioactive compounds of the group consisting of Ingenol, Ingenol esters and/or Tiglian-3-one derivatives of interest are recovered, such as e.g. only Ingenol, only one or more Ingenol esters or only one or more Tiglian-3-one derivatives.

Methods of harvest of suspension cultures are well known in the art. For example devices capable of separating biomass from supernatant (culture medium) can be employed, thus allowing separate processing of biomass and culture medium. Biomass can be separated at production scale e.g. by using a GEA Westfalia Continuous Separator Type CSC 20-06-476, capacity 2 m$^3$/hr, 8320 rpm, 81 bowl volume. The unit is suitable for sanitisation, cleaning in place and cooling. The supernatant can be collected using a 2.5 m$^3$ temperature-controlled holding tank; solid will be discharged semi continuously via a diaphragm pump.

Cell material/biomass and/or supernatant can be used directly for extraction or can be lyophilised in advance to the extraction procedure. Other methods known in the art can be used in order to prepare cell material or suspension material for the appropriate extraction method. The bioactive compounds of the group consisting of Ingenol, Ingenol esters and/or Tiglian-3-one derivatives can be recovered by any method known in the art including, without limitation, extraction using a non-aqueous polar or non-polar solvent, extraction using an acid medium, extraction using a basic medium, and recovery by resin absorption where the resin is either inside or outside of the culture vessel. As is shown e.g. in Examples 18 and 19, resin adsorption within the cell culture enables the extraction of the bioactive compounds without the prior need to harvest the biomass/supernatant, thereby greatly facilitating compound extraction while at the same time continuing the cell culture.

Methods of isolating the bioactive compounds of the group consisting of Ingenol, Ingenol esters and/or Tiglian-3-one derivatives produced comprise, without being limiting, method steps such as extraction of wet biomass, freeze dried cells or aqueous cell suspensions using organic solvents like e.g. methanol, ethyl acetate, acetone or toluene, followed by liquid-liquid extraction and/or a subsequent chromatographic separation by using e.g. liquid chromatography (LC), reversed phase LC, or liquid/liquid chromatography. An example for the solid phase matrix used in column chromatography is polyamide. Such methods of isolating the bioactive compounds have been described in the art. For example, if Ingenol-3-angelate is to be recovered, the purification steps described in Vasas et al. 2012 [Vasas et al. 2012; European Journal of Organic Chemistry; 5115-5130] can be employed. Where the compound to be recovered is 12-tigloyl-13-(2-methylbutanoyl)-6,7-epoxy-4,5,9,12,13, 20-hexahydroxy-1-tigliaen-3-one, the purification steps described in WO2007/070985 A1 can be employed. Finally, Ingenol can for example be isolated and the yield can even be enriched by applying the method described in WO2013/050365 A1.

Preferably, the Ingenol, Ingenol esters and/or Tiglian-3-one derivatives recovered in step (b) possess therapeutic activity, or can be modified to yield bioactive compounds having a therapeutic activity. Therapeutic activity can be mediated via regulation of protein kinase C (PKC) activity or independently from protein kinase C activity. Preferably, the Ingenol, Ingenol esters and/or Tiglian-3-one derivatives, or the bioactive compounds derived therefrom, are characterized in that they regulate protein kinase C activity. The term "regulation of protein kinase C activity", as used herein, includes the activation of protein kinase C as well as modifications of its functions such as e.g. enhancement of its activity. Preferably, the compounds recovered in step (b) of the method of the invention are capable of activating protein kinase C. The protein kinase C family of serine/threonine kinases plays a central role in mediating the signal transduction of extracellular stimuli that result in production of the second messenger diacylglycerol. The profound role of PKCs in the regulation of cell proliferation, differentiation, survival, and apoptosis makes them interesting drug targets [O'Brian et al. 2001; Cancer Metastasis Reviews: 20, 95-100]. Ingenol, Ingenol esters and/or Tiglian-3-one derivatives are known as activators of protein kinase C. For example, binding to protein kinase C and its activation by Ingenol has been reported by Haler et al. 1992 [Haler et al. 1992; Cancer Research: 52, 202-208]. The Interaction of Ingenol-3-angelate with protein kinase C has been described for example by Kedei et al. 2004 [Kedei et al. 2004; Cancer Research: 64, 3243-3255]. Protein kinase C activation by a member of Tiglian-3-one derivatives, the compound 12-tigloyl-13-(2-methylbutanoyl)-6,7-epoxy-4,5,9,12,13,20-hexahydroxy-1-tigliaen-3-one, has been described for example by Boyle et al. 2014 [Boyle et al. 2014; PLoS ONE: 9, e108887].

Assays for the determination of protein kinase C activity are well known in the art, such as e.g. the protein kinase assay as described in Kedei et al. 2004 [Kedei et al. 2004; Cancer Research: 64, 3243-3255] or as described in Boyle et al. 2014 [Boyle et al. 2014; PLoS ONE: 9, e108887].

Preferably, the Ingenol, Ingenol esters and/or Tiglian-3-one derivatives itself possesses therapeutic activity. Even more preferably, the Ingenol, Ingenol esters and/or Tiglian-3-one derivatives itself possesses therapeutic activity for use in treating a disease selected from the group consisting of skin cancers including melanomas, squamous cell carcinomas (SCC) & basal cell carcinomas (BCC), head & neck cancers, breast cancers, and prostate cancers.

In accordance with the present invention, a novel method is provided for the production of Ingenol, Ingenol ester and/or Tiglian-3-one derivatives. By using cells grown in a suspension culture, mass production of Ingenol, Ingenol ester and/or Tiglian-3-one derivatives is now possible, e.g. by semi-continuous or continuous cell culture techniques. No such plant cell culture approach for the mass production of Ingenol, Ingenol ester and/or Tiglian-3-one derivatives is presently available. The lack of such methods currently means that these bioactive compounds are isolated in small amounts only from harvested plants, because semi-synthetic and synthetic methods of producing these compounds are not available from an economic point of view, as discussed above.

The method of the present invention enables the isolation of increased amounts of these compounds as compared to the amounts previously reported to be isolated from plants. As is shown in example 6 (FIG. 9) below, at least 1.14 mg per liter of Ingenol-3-angelate suspension culture was obtained. As also detailed in example 6, this corresponds to an amount of 4.56 mg of Ingenol-3-angelate per kg fresh weight. In the prior art [Hohmann et al. 2000; Planta Medica: 66, 291-294], on the other hand, isolation methods from these plants were reported to result in only 1 mg Ingenol-3-angelate per 900 g fresh plant material (corresponding to approx. 1.1 mg/kg fresh plant material). Notably, in order to isolate these amounts in the prior art, plants had to be employed, whereas no expression of these compounds has been detected in in vitro cultures obtained from these plants. On the contrary, although prior art findings such as in Adolf et al. [Adolf et al. 1984; Planta Medica: 50, 259-261] describe the presence of diterpene esters of the ingenane type in the starting materials (e.g. the plant explants), these compounds were no longer present in the final callus cultures, thus suggesting that the expression of Ingenol and Ingenol esters is lost under in vitro culture conditions.

Thus, the present findings show for the first time that Ingenol-3-angelate, as a representative for ingenol esters, can in fact be obtained in in vitro culture conditions, and that the amounts obtainable thereby are superior to the amounts obtainable by extractions from plants, as previously relied on.

Accordingly, in a preferred embodiment of the method of the invention, the cells in step (a) produce Ingenol-3-angelate at a concentration of at least 1.14 mg Ingenol-3-angelate per liter suspension culture, more preferably at least 1.5 mg Ingenol-3-angelate per liter suspension culture and most preferably at least 1.8 mg Ingenol-3-angelate per liter suspension culture, whereas in one liter of suspension culture an amount of biomass (on a fresh weight basis) of at least 150 g is present at the time of harvesting the cells. More preferably, an amount of biomass (on a fresh weight basis) of at least 200 g, and most preferably of at least 250 g per liter of suspension culture is present at the time of harvesting the cells.

By using the entire suspension culture for extraction of the Ingenol, Ingenol ester and/or Tiglian-3-one derivatives, both the compounds present in the supernatant as well as the compounds present within the cells can be obtained.

In an alternative preferred embodiment of the method of the invention, one kg fresh weight of the cells in step (a) produce Ingenol-3-angelate at an amount of at least 4.56 mg, more preferably at an amount of at least 6 mg Ingenol-3-angelate, and most preferably at an amount of at least 7.2 mg Ingenol-3-angelate. It will be appreciated that this amount is produced by the cells upon their culture in the suspension and, thus, includes the amount of Ingenol-3-angelate obtained from the supernatant as well as the amount obtained from the cells themselves.

The term "kg fresh weight", as used in accordance with the present invention, refers to the weight of the biomass present in the cell culture as determined after removal of the supernatant. Accordingly, only the weight of the cells themselves is measured. Preferably, the cells are harvested via vacuum filtration and the fresh weight of this vacuum-filtrated biomass is determined.

Preferably, the amount Ingenol-3-angelate indicated above is the combined amount determined by carrying out the steps of vacuum filtration, lyophilisation of the biomass, compound extraction and analysis by LC/MS or HPLC (in this order) and the amount determined from the supernatant.

In a preferred embodiment, the present invention provides a method of producing Ingenol, Ingenol esters and/or Tiglian-3-one derivatives, the method comprising the steps of:
(a) culturing plant cells obtained from a plant selected from the family Euphorbiaceae in a nutrient medium in a suspension cell culture, wherein the cells produce Ingenol, one or more Ingenol esters and/or one or more Tiglian-3-one derivatives and wherein the cell culture conditions comprise conditions of shaking, preferably at about 130 rpm, in darkness, at a temperature of about 23° C. to 27° C., preferably about 25° C. and wherein, optionally, the cell cultures are sub-cultured at regular intervals, preferably every 6-8 days; and
(b) recovering the Ingenol, the one or more Ingenol esters and/or the one or more Tiglian-3-one derivatives produced in (a), preferably after a continuous culture for about 12 to 16 days.

In another preferred embodiment of the method of the invention, the method further comprises prior to step (a) an additional step of: (a-0) culturing explants of a plant from the family Euphorbiaceae on semi-solid or solid medium, thereby obtaining friable callus material.

The term "friable callus material" refers to a substantially undifferentiated cell mass cultured on solid or semi-solid medium. Methods for friable callus material formation and callus propagation are generally known in the art. Non-limiting methods for obtaining a callus include, for example, surface sterilising plant source material, e.g., by washing thoroughly with clean water, using a disinfectant such as hypochlorite, using wetting agents such as Tween or Triton, using antibiotics, and/or using antifungal agents. Callus formation can be initiated from any viable part of the plant (also referred to herein as "plant explant"), preferably from root, stem or leave tissue of the plant. The plant source material can be an intact part of the plant, or a portion thereof. To obtain a friable callus, the plant source material is placed on the surface of solidified medium or semi-solid medium, and incubated in a sterile environment for about 1-12 weeks, until a mass of undifferentiated cells (the friable callus material) grows in proximity to the plant source material. After establishing the friable callus material, the cells are cultured in liquid nutrient medium in accordance with the method of the invention.

Culture conditions for friable callus propagation including media components, pH ranges, carbon sources, nitrogen sources, macro-salts and micro-salts, vitamins, and growth regulators are well known in the art and have been described, for instance, in WO 97/44476. In a preferred embodiment, friable callus propagation comprises using a gelling agent. Gelling agents include, for example, agar, hydrogels, gelatin, and Gelrite®. Charcoal can be used for removing wastes and undesirable organic compounds.

In a particularly preferred embodiment, friable callus propagation comprises initiation of friable callus material on medium comprising vitamins. In an alternative particularly preferred embodiment, friable callus propagation comprises cultivation of friable callus on medium comprising a mixture of thiamine hydrochloride, pyridoxine hydrochloride and nicotinic acid. The medium for initiation and propagation of friable callus for all embodiments of the present invention can be a solid medium or a semi-solid medium. Preferably, the medium for initiation and propagation of friable callus in accordance with the present invention is a solid medium. Sub-culturing techniques known in the art can be used for periodic serial transfer of portions of friable callus into a fresh source of nutrients. Preferably, the frequency of transferring calli is between 4 to 6 weeks.

In another preferred embodiment of the method of the invention, the nutrient medium in step (a) is supplemented with one or more chemical compounds inducing the biosynthetic pathway to Ingenol and/or Ingenol esters and/or Tiglian-3-one derivatives.

Chemical compounds capable of inducing the biosynthetic pathway to Ingenol and/or Ingenol esters and/or Tiglian-3-one derivatives include, without being limiting, the above described elicitors. After being added to the culture medium of a suspension culture of Euphorbiaceae cells, these compounds confer an increase of the concentration of Ingenol and/or Ingenol esters and/or Tiglian-3-one derivatives. The terms elicitors, enhancement reagents and stimulants, are used in accordance to the present invention interchangeably, and relate both to compounds of biological (or biotic) and non-biological (or abiotic) origin that cause the above described increase in secondary metabolism when added to plant cell cultures.

Non-limiting examples of microorganisms as elicitors, enhancement reagents and stimulants include *Botrytis cinerea*, *Phytophthora megasperma*, *Pinellas stripticum*, *Oligosporus* sp., *Pythium mamillatum*, *Pythium sylvaticum*, *Verticillium dahlia*, *Verticillium* sp., *Penicillium minioluteum*, *Phytophthora lateralis*, *Cytospora cincta*, *Cytospora*

*leucostoma, Alternaria brassicicola, Alternaria solani, Alternaria cucumerina, Botrytis squamosa, Cochliobolus heterostrophus, Colletotrichum trifolii, Colletotrichum orbiculare, Colletotrichum graminicola, Colletotrichum gloeosporioides, Cylindrocladium floridanum, Fusarium crookwellense, Fusarium heterosporium, Fusarium oxysporum f.* sp. *conglutinans, Fusarium oxysporum f.* sp. *lycopersici, Fusarium oxysporum f.* sp. *pisi, Gibberella zeae, Gaeumannomyces graminis* var. *tritici, Geotrichum* sp., *Leptosphaeria korrae, Nectria haematococca* MPVI, *Mycosphaerella pinodes, Ophiostoma ulmi, Phoma lingam, Phoma pinodella, Phytophthora infestans, Pythium aristosporum, Pythium graminicola, Pythium ultimum, Rhizoctonia solani, Sclerotinia* sp., *S. nodorum* D-45, *Trametes versicolor, Ustilago maydis* and *Venturia inaequalis.*

Non-limiting examples of microbial fractions or products as elicitors, enhancement reagents and stimulants include Chitosan, Cellulysin, Lichenan, Multifect XL, Glucomannan, Multifect $C_L$, Pleuran, Resinase, Glucan, Pulpxyme, Carboxymethylglucan, SP431, Hydroxymethylglucan, Pectinol, Sulfoethylglucan, Rapidase, Mannan, Klerzyme, Xylan, Chitinase, Mannobiose, Mannotriose, Mannopentaose and Mannotetraose.

Non-limiting examples of elicitors, enhancement reagents and stimulants as well as some naturally occurring biochemicals as elicitors, enhancement reagents and stimulants include Arachidonic acid, Elaidic acid, Cyclic AMP, Dibutyryl Cyclic AMP, Methyl jasmonate, Cis—Jasmone, Miconazol Ferulic acid, AMO-1618, Triton X-100, Benzoic acid and derivatives, Salicylic acid and derivatives, Propyl gallate, Sesamol, Chlorocholine chloride, 3,4-Dichlorophenoxy triethyl (amine), Chloroethylphosphonic acid, Diethyldithiocarbamic acid, Nordihydroguaiaretic acid, Dithiothreitol, Sodium metabisulfite, Potassium metabisulfite, b-Amino-DL-Phenylalanine, Vanadyl sulfate, Uniconazol, Paclobutrazol, Spermine, Spermidine, Putrescine, Cadavarine, Protamine Sulfate, SKF-7997, MER 29, Ancymidol, Triadimefon, Phosphon D, Thiourea, Dextran Sulfate, Hydroquinone, Chitosan glutamate, Fenpropemorph, Prochloraz, Naptifine, EDU, HTA, MPTA, Glutathione, EGTA, Gibberellins, Abscisic Acid, 1,3-Diphenyl urea, Diazolidinyl urea, Phloroglucinol, Sodium alginate and Carragenan.

Further non-limiting examples of elicitors, enhancement reagents and stimulants include DCPTA, DIPTA, ACC, Brassinosteroids, BHA, BHT, OTA, Potassium pyrophosphate, p-Aminohippuric acid, Sodium pyrophosphate, Benzylcinnamate, Uracil, Jasmonic acid, Melatonin, Hydroxylamine hydrochloride, Dihydroisojasmone, Thionicotinamide, Isojasmone, S-adenosyl-L-methionine, Inosine triphosphate, Tetrahydrojasmone, Indole-3-lactic acid, Lactone of cis-jasmone, Indole-3-pyruvic acid, Dihydrojasmone, Indole-2-carboxylic acid, Jasminolactone, Indole-3-aldehyde, Jasmolactone, N-indolyl acetyl valine, 12-Oxophytodienoic acid, Pyridoxal phosphate, Jasmonol, Methyl dihydrojasmonate, g-Methyldecalactone, Bipyridyl, Citronellyl tiglate, 4-Acetamidophenol, Jasmonyl acetate, Imidazole, Mastoparan, Octyl-β-D-glucopyranoside, Lysophosphatidic acid, 3-Aminopyridine, Cypermethrin, Guanylic acid, Cantharidin, Citydylic acid, Acetylsalicylic acid, Isopropyl-β-d-thiogalactopyranoside, 3-(4-hydroxyphenyl) propionic acid, 2,6-Dichloroisonicotinic acid, 3-(2-Hyroxyphenyl) propionic acid, Nitric oxide, Traumatic acid, Thiobenzoic acid, Citric acid, Dimethylaminophenylalanine, Cytidylic acid, p-Hydroxyphenylpyruvic acid, Malic acid or Malic acid salt, 2,3-Dihydroxybenzoic acid, Potassium malate, Ethyl benzoate, Citric acid salts and derivatives, 3,4-Dihydroxycinnamic acid, Flavin adenine mononucleotide, 4-Hydroxycinnamic acid, Flavin monocleotide, N-acetyl-L-phenylalanine, 3-Benzoylpropionic acid, p-Hydroxycinnamic acid, 5', 5'-Dithiobis (2-nitrobenzoic acid), 13-Hydroxypyruvic acid, 4-Hydroxyphenylpyruvic acid, S-Adenosylmethionine, Methyl cinnamate, Pyridoxal phosphate, Methyl salicylate, 6-Aminonicotinamide, 2-Napthylbenzoate, 4-Dimethylaminopyridine, Phenylsalicylate, N-(2-Hydroxyethyl)succinimide, Thiosalicylic acid, 2-oxoglutaric acid, Propachlor, Thiamine, Vinyl propionate, Triethylamine hydrochloride, 3,5-Diisopropylsalicylic acid, Adenine sulfate, p-Amino-L-Phenylalanine, Benzyl salicylate, 1,2-Benzisoxazole, 2,4-Carbonyldibenzoic acid, L-Citrulline, D-Erythrose 4-Phosphate, Fructose 1,6-Diphosphate, Inosine triphosphate, N-Methylputrescine dihydrochloride, β-Phenylethylamine hydrochloride, Lysine, Guanylic acid, Melatonin, Aminocyclopropane-carboxylic acid, Isopentylpyrophosphate, N-Acetyl-L-glutamine, Isoglutamine, Threonine, Potassium Pyrophosphate, Sodium pyrophosphate, L-2-Aminoadipic acid, N-methyl-N-Propagylbenzylamine, hydrochloride, Aminoguanidine hemisulfate, L-(+)-2-Amino-7-Phosphonoheptanoic acid, Ammonium sulfamate, Spermine bis nitric oxide adduct, Diethylamine Bis nitric oxide adduct, Galactose, Valine, Vitamin B-12, Ascorbic acid and derivatives, Coronatine, Phenobarbital, Pregnenolone, 24-epi-Brassinolide, n-Propyl Dihydrojasmonate, Propyl jasmonate and Epimethyl jasmonate.

Further non-limiting examples of elicitors, enhancement reagents and stimulants include Xylanase, Butaclore, Chitooligosaccharides, Butylisothiocynate, Spermine bis nitric oxide Adduct, Chloramben, N,N'-Diacetylchitobiose isopropylamine bis, Ethyl carbamate, 2-Hydroxyethylhydrazine, Nitric oxide Adduct, Hydroxyglutaric acid disodium, Diethylamine Bis (Nitric oxide) Adduct, Tryptophol, Benzyl N,N'-Diacetyl-13-chitobioside, Thiourea, Syringic acid, Thioacetamide, Benzothiadiazole, 2,4,6-Trichlorphenol, Bipyridyl, Pyridine-2-aldoxime methochloride, Gossypol and derivatives, Potassium oxalate monohydrate, 2-chlor-4-methylisonicotinic acid, Poly-L-Lysine hydrobromide, Indomethacin, Nerol, N,N',N'-Triacetylchitotriose, N-(1-Naphthyl) phthalamic acid, N,N'-Diacitylchitobiose, Oxalate, Diammoniun oxalate, Octapomine hydrochloride, Nigeran, Oxizamide, p-hydroxyacetophenone, 2-Methylpyrazine, Pectic acid, Methoxyacetic acid, Lysozyme, N-Ethoxycarbonyl-2-ethoxy-1,2-Dihydroquinoline, Nitric oxide, Glutathione (reduced), Lanthanum acitate, 1,2-Diaminopropane, Linolenic acid, 1,3-Diaminopropane, Lipase, β-mercaptoethylamine, Iodoacetamide, Hydroxylamine, 2-Hydroxyethylhydrazine, Deoxyglucose, Dinocap, 2-Chlorobenzoic acid, 1,3-Diphenylurea, 2-Methyl-1,2-DL (3-Pyridyl) 1-Propane, Hydrogen peroxide, 5-Bromouracil, Urea hydroperoxide, 7-Nitrondazole, Sebacic acid, 8-Hydroxyquinoline, Benzoyl peroxide, Acedoamidocinnamic acid, N-methylmaleimide, 2-Aminoanthraquinone, Cumen peroxide, N-acetyl-L-glutamic acid, N-acetyl-D-Glucosamine, Agmatin, Octyl-β-D-Glucopyranoside, 3-Acetyl pyridine, Diisopropyl fluorophosphates, Butyryl Lactate, Isopropyl-β-D-thiogalactopyranoside, 7-Bromo-5-chloro-8-hydroxyquinoline, Hydroxyethyl-β-1,3-glucan, Benzylbenzoate, Dextran, Bromoxynil, Lucifer yellow, Syringaldehyde, Chitinase, Bacitracin, Calcium cyanide, Glucans, Glutaric acid, Morpholine, Octamethylcyclotetrasiloxane, Trigonelline hydrochloride, Anthranilic acid, Colistin methane sulfonate, Colchicine, 2,4-Dichlorophenol, L-Phenylalanine-2-naphthylamide, Hydroxyglutaric acid, and its salts, DL-2-Hydroxy-3-methylbutyric acid, 1-10-Phenanthroline monohydrate, N-sulfosuccinimidyl-3-(4-hydroxyphenyl)propionate, Trans-1,6-diphenylhexatriene, Urea hydrogen peroxide, Hydrogen peroxide, Bestatin, Butylated hydroxyanisole, Butylated hydroxytoluene, Gellan gum, cellulase, Pimelic acid, Diisopropyl phosphochloridate, Nitrapyrin, t-Butyl hydroperoxide, DL-Phosphinothricin ammonium, Methyl syringate, Trifluralin, Tridecanone, Mimosine, Narigenin, Dimethylaminopyridine, 1-Benzylimidazole, DL-o-chlorophenylalanine, Cetylpyridinium chloride, Hydroquinone and Syringomycin. All these compounds have been described e.g. in EP 1 398 384.

Preferred elicitors, enhancement reagents and stimulants in accordance with this embodiment of the invention include, without being limiting, salicylic acid and methyl jasmonate.

In a further preferred embodiment of the method of the invention, the plant selected from the family Euphorbiaceae is a plant of the genus *Euphorbia*. More preferably, the plant of the genus *Euphorbia* is a plant of the species *Euphorbia peplus*, *Euphorbia lathyris* or *Euphorbia epithymoides*. Most preferably, the plant of the genus *Euphorbia* is a plant of the species *Euphorbia peplus* or *Euphorbia lathyris*.

Ingenol and Ingenol esters have been detected in various parts of plants representing members of the genus *Euphorbia*, such as e.g. *Euphorbia peplus*, *Euphorbia lathyris*, *Euphorbia antiquorum*, *Euphorbia helioscopia*, *Euphorbia paralias*, *Euphorbia drummondii* and *Euphorbia hirta* [Hohmann et al. 2000; Planta Medica: 66, 291-294]. At present, Ingenol is most commonly obtained by extraction from seeds of *Euphorbia lathyris*. Ingenol-3-angelate is most commonly obtained from *Euphorbia peplus*.

In a more preferred embodiment of the method of the invention, the compound(s) recovered in (b) are Ingenol and/or one or more Ingenol esters. Thus, it is particularly preferred that in those cases where the plant selected from the family Euphorbiaceae is a plant of the genus *Euphorbia*, the compound(s) recovered in step (b) in accordance with the method of the invention are Ingenol and/or one or more Ingenol esters.

Accordingly, in a preferred embodiment, the invention relates to a method of producing Ingenol, the method comprising the steps of:
(a) culturing plant cells obtained from a plant selected from the genus *Euphorbia* in a nutrient medium in a suspension cell culture, wherein the cells produce Ingenol; and
(b) recovering the Ingenol produced in (a).

In an alternative preferred embodiment, the invention relates to a method of producing one or more Ingenol esters, the method comprising the steps of:
(a) culturing plant cells obtained from a plant selected from the genus *Euphorbia* in a nutrient medium in a suspension cell culture, wherein the cells produce one or more Ingenol esters; and
(b) recovering the one or more Ingenol esters produced in (a).

In another preferred embodiment, the invention relates to a method of producing Ingenol, the method comprising the steps of:
(a) culturing plant cells obtained from a plant of the species *Euphorbia peplus* in a nutrient medium in a suspension cell culture, wherein the cells produce Ingenol; and
(b) recovering the Ingenol produced in (a).

In an alternative preferred embodiment, the invention relates to a method of producing one or more Ingenol esters, the method comprising the steps of:
(a) culturing plant cells obtained from a plant of the species *Euphorbia peplus* in a nutrient medium in a suspension cell culture, wherein the cells produce one or more Ingenol esters; and
(b) recovering the one or more Ingenol esters produced in (a).

In a further preferred embodiment, the invention relates to a method of producing Ingenol, the method comprising the steps of:
(a) culturing plant cells obtained from a plant of the species *Euphorbia lathyris* in a nutrient medium in a suspension cell culture, wherein the cells produce Ingenol; and
(b) recovering the Ingenol produced in (a).

In yet a further alternative preferred embodiment, the invention relates to a method of producing one or more Ingenol esters, the method comprising the steps of:
(a) culturing plant cells obtained from a plant of the species *Euphorbia lathyris* in a nutrient medium in a suspension cell culture, wherein the cells produce one or more Ingenol esters; and
(b) recovering the one or more Ingenol esters produced in (a).

In a further preferred embodiment, the invention relates to a method of producing Ingenol, the method comprising the steps of:
(a) culturing plant cells obtained from a plant of the species *Euphorbia epithymoides* in a nutrient medium in a suspension cell culture, wherein the cells produce Ingenol; and
(b) recovering the Ingenol produced in (a).

In yet a further alternative preferred embodiment, the invention relates to a method of producing one or more Ingenol esters, the method comprising the steps of:
(a) culturing plant cells obtained from a plant of the species *Euphorbia epithymoides* in a nutrient medium in a suspension cell culture, wherein the cells produce one or more Ingenol esters; and
(b) recovering the one or more Ingenol esters produced in (a).

In another more preferred embodiment of the method of the invention, the compound recovered in step (b) is Ingenol-3-angelate and the nutrient medium in step (a) is supplemented with angelic acid.

As is shown in the appended examples, addition of angelic acid (2-methyl-2(Z)-butenoic acid) to the nutrient medium resulted in an enhanced production of Ingenol-3-angelate. Preferably, angelic acid is added to the culture medium at a concentration between 1 μM and 5 mM, more preferably between 100 μM and 4 mM such as e.g. between 300 μM and 3 mM and most preferably the concentration added to the nutrient medium is about 0.5 mM. Angelic acid can be commercially obtained, e.g. from TCI Deutschland GmbH.

Accordingly, in a preferred embodiment, the invention relates to a method of producing Ingenol-3-angelate, the method comprising the steps of:
(a) culturing plant cells obtained from a plant selected from the family Euphorbiaceae in a nutrient medium supplemented with about 0.5 mM angelic acid in a suspension cell culture, wherein the cells produce Ingenol-3-angelate; and
(b) recovering the Ingenol-3-angelate produced in (a).

In a more preferred embodiment, the invention relates to a method of producing Ingenol-3-angelate, the method comprising the steps of:
(a) culturing plant cells obtained from a plant selected from the genus *Euphorbia* in a nutrient medium supplemented with about 0.5 mM angelic acid in a suspension cell culture, wherein the cells produce Ingenol-3-angelate; and (b) recovering the Ingenol-3-angelate produced in (a).

In a yet further preferred embodiment, the invention relates to a method of producing Ingenol-3-angelate, the method comprising the steps of:

(a) culturing plant cells obtained from a plant of the species *Euphorbia peplus* in a nutrient medium supplemented with about 0.5 mM angelic acid in a suspension cell culture, wherein the cells produce Ingenol-3-angelate; and (b) recovering the Ingenol-3-angelate produced in (a).

In an alternative further preferred embodiment, the invention relates to a method of producing Ingenol-3-angelate, the method comprising the steps of:

(a) culturing plant cells obtained from a plant of the species *Euphorbia lathyris* in a nutrient medium supplemented with about 0.5 mM angelic acid in a suspension cell culture, wherein the cells produce Ingenol-3-angelate; and (b) recovering the Ingenol-3-angelate produced in (a).

In a further alternative further preferred embodiment, the invention relates to a method of producing Ingenol-3-angelate, the method comprising the steps of:

(a) culturing plant cells obtained from a plant of the species *Euphorbia epithymoides* in a nutrient medium supplemented with about 0.5 mM angelic acid in a suspension cell culture, wherein the cells produce Ingenol-3-angelate; and (b) recovering the Ingenol-3-angelate produced in (a).

In an alternative preferred embodiment of the method of the invention, the plant selected from the family Euphorbiaceae is a plant of the genus *Fontainea* or *Hylandia*. More preferably, the plant of the genus *Fontainea* or *Hylandia* is a plant selected from the group consisting of *Fontainea picrosperma*, *Fontainea venosa* and *Hylandia dockrillii*.

As discussed herein above, plants or plant parts of the genus *Fontainea* or *Hylandia*, in particular the species *Fontainea picrosperma*, *Fontainea venosa* or *Hylandia dockrillii*, are currently used as the source to obtain Tiglian-3-one derivatives.

In a more preferred embodiment of the method of the invention, the compound(s) recovered in (b) is/are one or more Tiglian-3-one derivatives. Thus, it is particularly preferred that in those cases where the plant selected from the family Euphorbiaceae is a plant of the genus *Fontainea* or *Hylandia*, the compound(s) recovered in step (b) in accordance with the method of the invention is/are one or more Tiglian-3-one derivatives.

Accordingly, in a preferred embodiment, the invention relates to a method of producing one or more Tiglian-3-one derivatives, the method comprising the steps of:

(a) culturing plant cells obtained from a plant selected from the genus *Fontainea* in a nutrient medium in a suspension cell culture, wherein the cells produce one or more Tiglian-3-one derivatives; and (b) recovering the one or more Tiglian-3-one derivatives produced in (a).

In an alternative preferred embodiment, the invention relates to a method of producing one or more Tiglian-3-one derivatives, the method comprising the steps of:

(a) culturing plant cells obtained from a plant selected from the genus *Hylandia* in a nutrient medium in a suspension cell culture, wherein the cells produce one or more Tiglian-3-one derivatives; and (b) recovering the one or more Tiglian-3-one derivatives produced in (a).

In another preferred embodiment, the invention relates to a method of producing one or more Tiglian-3-one derivatives, the method comprising the steps of:

(a) culturing plant cells obtained from a plant of the species *Fontainea picrosperma* in a nutrient medium in a suspension cell culture, wherein the cells produce one or more Tiglian-3-one derivatives; and (b) recovering the one or more Tiglian-3-one derivatives produced in (a).

In an alternative preferred embodiment, the invention relates to a method of producing one or more Tiglian-3-one derivatives, the method comprising the steps of:

(a) culturing plant cells obtained from a plant of the species *Fontainea venosa* in a nutrient medium in a suspension cell culture, wherein the cells produce one or more Tiglian-3-one derivatives; and (b) recovering the one or more Tiglian-3-one derivatives produced in (a).

In an alternative preferred embodiment, the invention relates to a method of producing one or more Tiglian-3-one derivatives, the method comprising the steps of:

(a) culturing plant cells obtained from a plant of the species *Hylandia dockrillii* in a nutrient medium in a suspension cell culture, wherein the cells produce one or more Tiglian-3-one derivatives; and (b) recovering the one or more Tiglian-3-one derivatives produced in (a).

It is particularly preferred in accordance with these embodiments of the method of the invention of producing one or more Tiglian-3-one derivatives that the Tiglian-3-one derivative is 12-tigloyl-13-(2-methylbutanoyl)-6,7-epoxy-4,5,9,12,13,20-hexahydroxy-1-tigliaen-3-one (EBC-46).

The present invention further relates to a plant suspension cell culture, wherein the cells are cells obtained from a plant selected from the family Euphorbiaceae, and wherein the plant cells produce Ingenol and/or one or more Ingenol ester and/or one or more Tiglian-3-one derivatives.

Preferably, these suspension cell cultures are cultured/produced/producible/provided according to any one of the embodiments described herein above.

The definitions and preferred embodiment provided herein above with regard to the method of the invention apply mutatis mutandis also to this suspension cell culture of the present invention.

To the inventors' best knowledge, no suspension cell culture of plant cells of the family Euphorbiaceae is available in the art that is capable of producing Ingenol and/or one or more Ingenol esters and/or one or more Tiglian-3-one derivatives. Based on the method of the present invention, such a suspension cell culture could now be provided for the first time and is suitable for the mass production of these compounds.

The present invention further relates to a plant cell biomass comprising plant cells obtained or obtainable from the suspension cell culture of the invention, and comprising Ingenol and/or one or more Ingenol esters and/or one or more Tiglian-3-one derivatives.

Again, all definitions and preferred embodiment provided herein above with regard to the method of the invention apply mutatis mutandis also to this plant cell biomass of the present invention.

The term "biomass", as used herein, refers to the biological material making up the cell mass of the suspension culture. In other words, when the cells of the suspension cell culture are separated from the liquid medium, the biomass is obtained. The term "biomass", as used herein, refers to a freshly obtained biomass, but also to a biomass that has been stored, e.g. in form of a frozen biomass, cryopreserved biomass or lyophilised powder.

The biomass, in accordance with the invention, comprises Ingenol, Ingenol esters and/or one or more Tiglian-3-one derivatives. Accordingly, the biomass of the present invention represents a valuable source of these compounds, which can be isolated from the biomass.

The present invention further relates to cryopreserved cells of a plant suspension cell culture of the invention.

Cryopreserved cells can be prepared by first adding a cryoprotectant and subsequently freezing the plant cell suspension cultures of the invention.

The term "cryopreservation", as used herein, relates to a method of preserving the cells of interest by cooling them to sub-zero temperatures. At sufficiently low temperatures, enzymatic and/or chemical activities that would normally cause damage to the cells are halted. The essence of cryopreservation is to effect cell dehydration and concentration of the cytosol in a controlled and minimally injurious manner so that crystallization in the cytosol is precluded or minimized during quenching in liquid nitrogen. With conventional cryopreservation procedures, the specimens (cells and/or tissues) are equilibrated in a solution containing a cryoprotectant. The suspension is cooled and seeded with an ice crystal at a temperature slightly below its freezing point. Subsequently, the suspension is cooled at an optimum rate to an intermediate subzero temperature (e. g. −30 to −40° C.) prior to quenching in liquid nitrogen. During ice formation in the suspending medium, solutes are excluded from the ice matrix and are concentrated in an unfrozen fraction of the suspending medium.

The term "cryoprotectant", in accordance with the present invention, relates to compounds that are suitable to protect the cells in the subsequent freezing steps. Cryoprotectants function by increasing the solute concentration in cells. In order to be biologically viable, cryoprotectants must easily penetrate cells and must not be toxic to cells. Non-limiting examples of cryoprotectants include glycols, such as ethylene glycol, propylene glycol, and glycerol, as well as dimethyl sulfoxide (DMSO). Preferably, the cryoprotectants employed in accordance with the present invention are dimethyl sulfoxide (DMSO) or glycerol.

The definitions and preferred embodiment provided herein above with regard to the method of the invention as well as the suspension culture and the plant cell biomass of the invention apply mutatis mutandis also to these cryopreserved cells of a plant suspension cell culture of the present invention.

Cryopreserved Euphorbiaceae cells capable of producing Ingenol, Ingenol esters and Tiglian-3-one derivatives in accordance with the present invention have a high level of restoration of cellular function following thawing of the cryopreserved plant cells. Preferably, more than 50% of viable cells capable of producing Ingenol, Ingenol esters and Tiglian-3-one derivatives are recovered following thawing of the cryopreserved Euphorbiaceae cells; more preferably more than 75% of viable cells capable of producing Ingenol, Ingenol esters and Tiglian-3-one derivatives are recovered following thawing of the cryopreserved Euphorbiaceae cells.

The present invention further relates in a preferred embodiment to the method of the invention of producing Ingenol, Ingenol esters and/or Tiglian-3-one derivatives, wherein the plant cells for culture in step (a) are obtained from the cryopreserved cells according to the invention.

In accordance with this embodiment, the method of the invention of producing Ingenol, Ingenol esters and/or Tiglian-3-one derivatives comprises the steps of:
(A) recovering (a) viable plant cell(s) from the cryopreserved cells according to the invention;
(B) propagating cells from the viable cell(s) of (A);
(C) culturing said cells obtained in (B) in a nutrient medium in a suspension cell culture, wherein the cells produce Ingenol, one or more Ingenol esters and/or one or more Tiglian-3-one derivatives; and
(D) recovering the Ingenol, the one or more Ingenol esters and/or the one or more Tiglian-3-one derivatives produced in (C).

In accordance with this embodiment of the method of the invention, the cryopreserved cells of the invention are thawed in a first step, thereby recovering viable cells capable of producing Ingenol, Ingenol esters and Tiglian-3-one derivatives.

To this end, cryo-vials comprising cryopreserved Euphorbiaceae cells capable of producing Ingenol, Ingenol esters and Tiglian-3-one derivatives can be thawed in a water bath or another sustained temperature environment at a temperature in the range of about 37° C. to about 45° C. Preferably, the cells are thawed at a temperature of about 45° C. in a water bath or another sustained temperature environment with occasional agitation or gentle stirring for about 90 seconds or until the frozen cells have thawed.

Once the cells are thawed, the cells are transferred to nutrient medium for the propagation of cells. It will be appreciated that the propagation of cells can be in the form of a suspension cell culture, or in the form of calli.

For example, to prepare callus material from the thawed cells, the thawed solution is washed and the biomass is separated from the solution. The washed biomass is then plated out on solid nutrient medium and incubated in darkness until callus material is obtained. This callus material may subsequently be used as the starting material for the various embodiments of the invention.

Preferably, the method is as follows: The thawed solution is poured into 10 ml washing solution, preferably a solution comprising 0.25 M sorbitol and 0.0025 M $CaCl_2 \times 2H_2O$. Following incubation, the biomass is separated from the solution. Preferably, the incubation is carried out for about 5 to 25 minutes, more preferred for about 10 to 20 minutes, and most preferably the incubation is carried out for about 15 minutes. The washed biomass is then plated out on solid MS-medium, preferably an MS-medium comprising half strength MS basal salt, 2% sucrose, supplemented with 0.5 mg/l BAP and 0.5 mg/l 2,4-D. Plates are then incubated in darkness at 25±2° C. After several weeks, recovered callus material is obtained. Preferred but not limiting recovering time according to the invention is between about 4 weeks to about 16 weeks.

Alternatively, the thawed cells are transferred into liquid nutrient medium and are propagated in form of a suspension culture.

Preferably, an intermediate step is included during the propagation in step (B) which includes testing the recovered cells for the production of Ingenol, Ingenol esters and/or Tiglian-3-one derivatives, in order to confirm that cells recovered are still capable of producing said compounds. Means and methods for determining the production of Ingenol, Ingenol esters and/or Tiglian-3-one derivatives have been described herein above.

Finally, in a last step, Ingenol, Ingenol esters and/or Tiglian-3-one derivatives are recovered from the cell culture as described above.

In a further preferred embodiment of the method of the invention or the plant suspension cell culture of the invention, one kg (fresh weight) of cells produce at least 4.56 mg Ingenol-3-angelate, preferably at least 6 mg Ingenol-3-angelate, and most preferably at least 7.2 mg Ingenol-3-angelate. As discussed herein above, these amounts refer to the amount produced by said cells, i.e. the combined amount of Ingenol-3-angelate obtained from the cells in the biomass as well as from the supernatant.

In an alternative further preferred embodiment of the method of the invention or the plant suspension cell culture of the invention, the cells produce Ingenol-3-angelate at a concentration of at least 1.14 mg Ingenol-3-angelate per liter suspension culture, more preferably at least 1.5 mg Ingenol-3-angelate per liter suspension culture and most preferably at least 1.8 mg Ingenol-3-angelate per liter suspension culture, whereas in one liter of suspension culture an amount of biomass (on a fresh weight basis) of at least 150 g is present at the time of harvesting the cells. More preferably, an amount of biomass (on a fresh weight basis) of at least 200 g, and most preferably of at least 250 g per liter of suspension culture is present at the time of harvesting the cells.

The definitions and preferred embodiments described herein above apply mutatis mutandis to these preferred embodiments.

It will be appreciated that all method steps described herein are carried out in the described order, i.e. step (a) is carried out prior to step (b). Where an additional step (a-0) is included, this step is carried out first, prior to step (a). In other words, the claimed methods comprise (or consist of) a first step (a) and a subsequent step (b) or, alternatively, a first step (a-0), a subsequent step (a) and third step (b) subsequent to step (a). The same applies to steps (A) to (D) of the method of the invention of producing Ingenol, Ingenol esters and/or Tiglian-3-one derivatives using cryopreserved cells.

Unless otherwise defined, all technical and scientific terms used herein have the same meaning as commonly understood by one of ordinary skill in the art to which this invention belongs. In case of conflict, the patent specification, including definitions, will prevail.

As regards the embodiments characterised in this specification, in particular in the claims, it is intended that each embodiment mentioned in a dependent claim is combined with each embodiment of each claim (independent or dependent) said dependent claim depends from. For example, in case of an independent claim 1 reciting 3 alternatives A, B and C, a dependent claim 2 reciting 3 alternatives D, E and F and a claim 3 depending from claims 1 and 2 and reciting 3 alternatives G, H and I, it is to be understood that the specification unambiguously discloses embodiments corresponding to combinations A, D, G; A, D, H; A, D, I; A, E, G; A, E, H; A, E, I; A, F, G; A, F, H; A, F, I; B, D, G; B, D, H; B, D, I; B, E, G; B, E, H; B, E, I; B, F, G; B, F, H; B, F, I; C, D, G; C, D, H; C, D, I; C, E, G; C, E, H; C, E, I; C, F, G; C, F, H; C, F, I, unless specifically mentioned otherwise.

Similarly, and also in those cases where independent and/or dependent claims do not recite alternatives, it is understood that if dependent claims refer back to a plurality of preceding claims, any combination of subject-matter covered thereby is considered to be explicitly disclosed. For example, in case of an independent claim 1, a dependent claim 2 referring back to claim 1, and a dependent claim 3 referring back to both claims 2 and 1, it follows that the combination of the subject-matter of claims 3 and 1 is clearly and unambiguously disclosed as is the combination of the subject-matter of claims 3, 2 and 1. In case a further dependent claim 4 is present which refers to any one of claims 1 to 3, it follows that the combination of the subject-matter of claims 4 and 1, of claims 4, 2 and 1, of claims 4, 3 and 1, as well as of claims 4, 3, 2 and 1 is clearly and unambiguously disclosed.

The above considerations apply mutatis mutandis to all appended claims. To give a non-limiting example, the combination of claims 8 and 1 is clearly and unambiguously envisaged in view of the claim structure. The same applies for example to the combination of claims 8, 1 and 2, or 8, 7 and 1, etc.

The foregoing detailed description describes the invention with reference to specific exemplary embodiments. However, it will be appreciated that various modifications and changes can be made without departing from the scope of the present invention as set forth in the appended claims. The detailed description and accompanying drawings are to be regarded as merely illustrative, rather than as restrictive, and all such modifications or changes, if any, are intended to fall within the scope of the present invention as described and set forth herein.

More specifically, while illustrative exemplary embodiments of the invention have been described herein, the present invention is not limited to these embodiments, but includes any and all embodiments having modifications, omissions, combinations (e.g., of aspects across various embodiments), adaptations and/or alterations as would be appreciated by those in the art based on the foregoing detailed description. The limitations in the claims are to be interpreted broadly based on the language employed in the claims and not limited to examples described in the foregoing detailed description or during the prosecution of the application, which examples are to be construed as non-exclusive.

The figures show:

FIG. 1: Ingenol recovered from biomass of an *Euphorbia peplus* cell suspension cultured in growth medium and harvested at day 7 and day 14, respectively.

Figure 2:
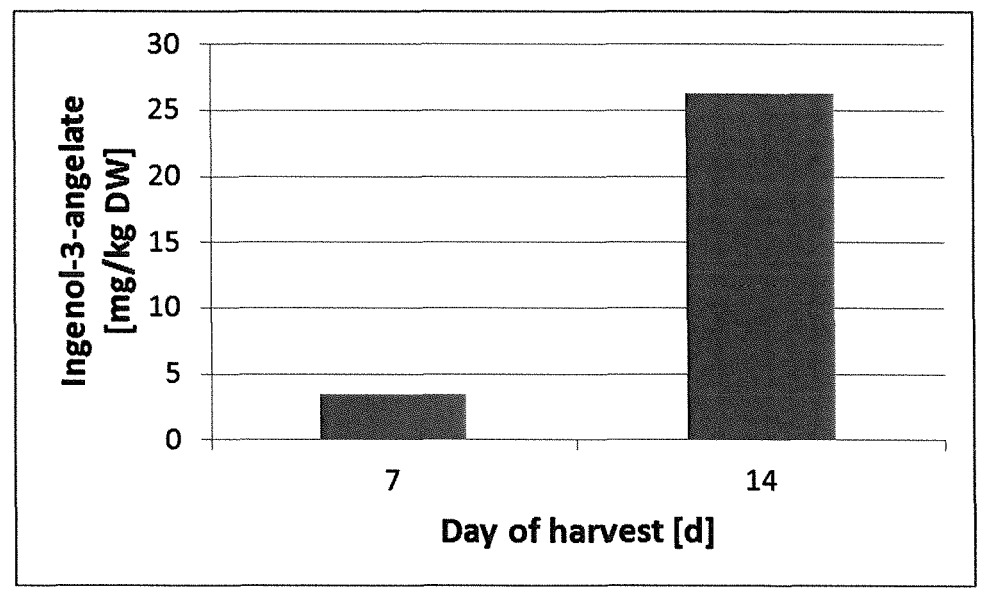

FIG. 2: Ingenol-3-angelate recovered from biomass of an *Euphorbia peplus* cell suspension cultured in growth medium and harvested at day 7 and day 14, respectively.

Figure 3:
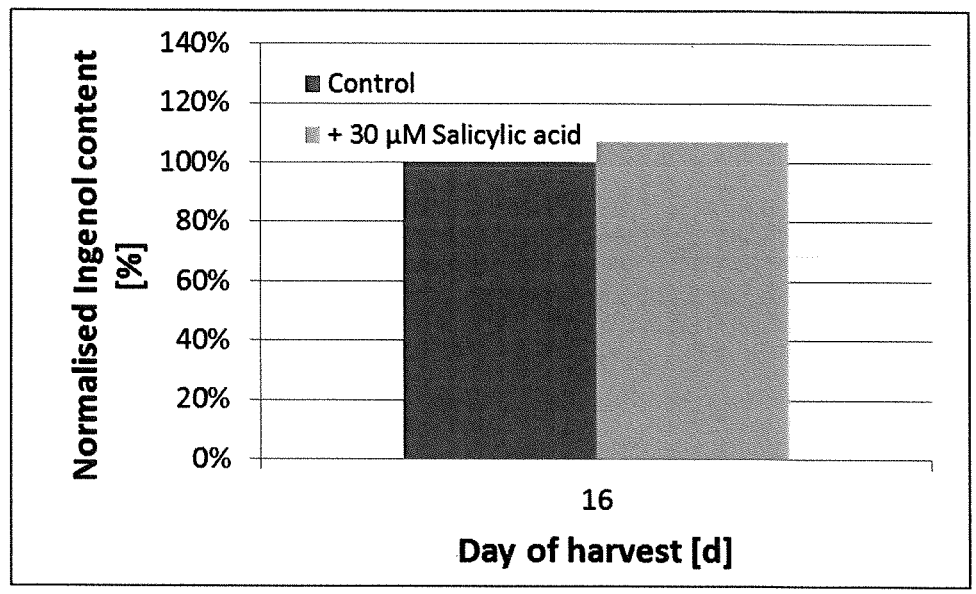

FIG. 3: Relation of Ingenol concentration recovered from biomass of an *Euphorbia peplus* cell suspension cultured in production medium supplemented with 30 μM salicylic acid and harvested at day 16 to Ingenol concentration recovered from biomass of an *Euphorbia peplus* cell suspension cultured in growth medium and harvested at day 16 (100%).

Figure 4:
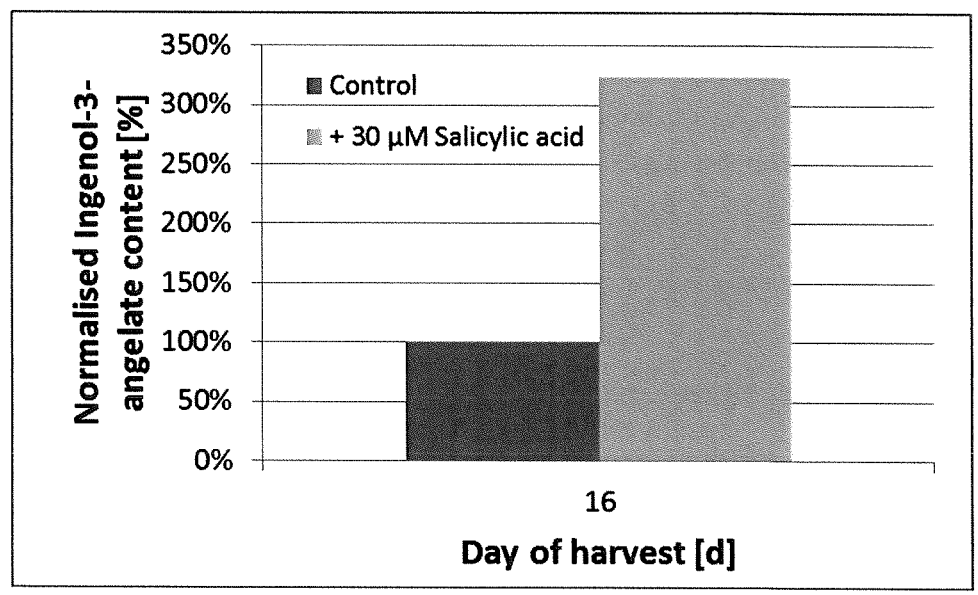

FIG. 4: Relation of Ingenol-3-angelate concentration recovered from biomass of an *Euphorbia peplus* cell suspension cultured in production medium supplemented with 30 μM salicylic acid and harvested at day 16 to Ingenol-3-angelate concentration recovered from biomass of an *Euphorbia peplus* cell suspension cultured in growth medium and harvested at day 16 (100%).

Figure 5:
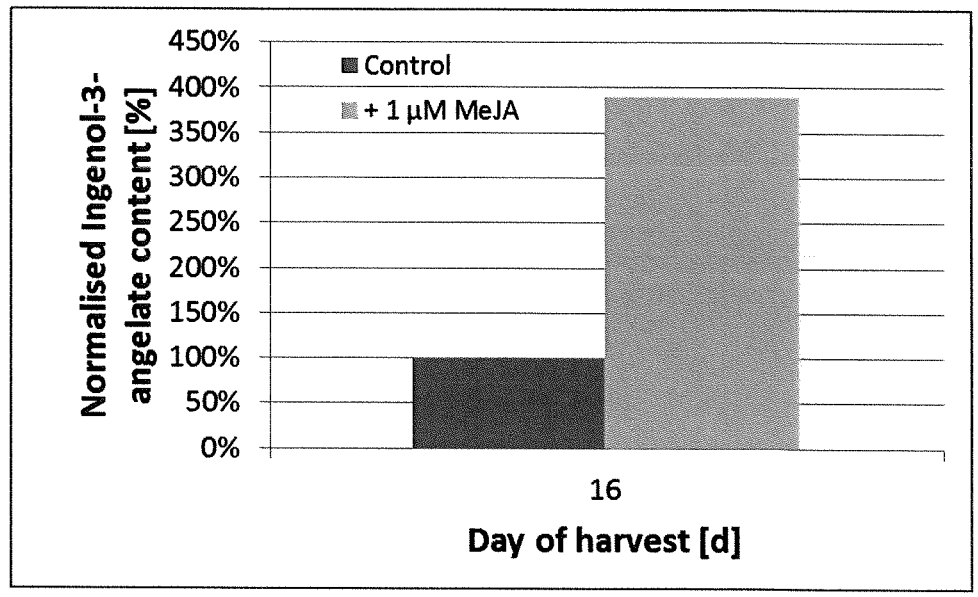

FIG. 5: Relation of Ingenol-3-angelate concentration recovered from biomass of an *Euphorbia peplus* cell suspension cultured in production medium supplemented with 1 μM methyl jasmonate (MeJA) and harvested at day 16 to Ingenol-3-angelate concentration recovered from biomass of an *Euphorbia peplus* cell suspension cultured in growth medium and harvested at day 16 (100%).

Figure 6:
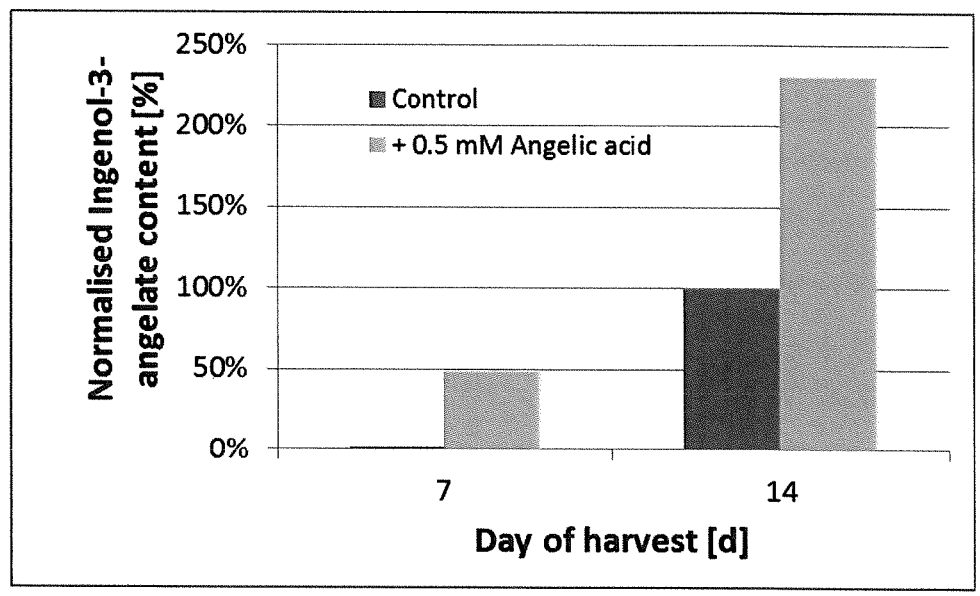

FIG. 6: Relation of Ingenol-3-angelate concentration recovered from biomass of an *Euphorbia peplus* cell suspension cultured in production medium supplemented with 0.5 mM angelic acid and harvested at day 7 and day 14 to Ingenol-3-angelate concentration recovered from biomass of an *Euphorbia peplus* cell suspension cultured in growth medium and harvested at day 7 and day 14 (100%).

Figure 7:
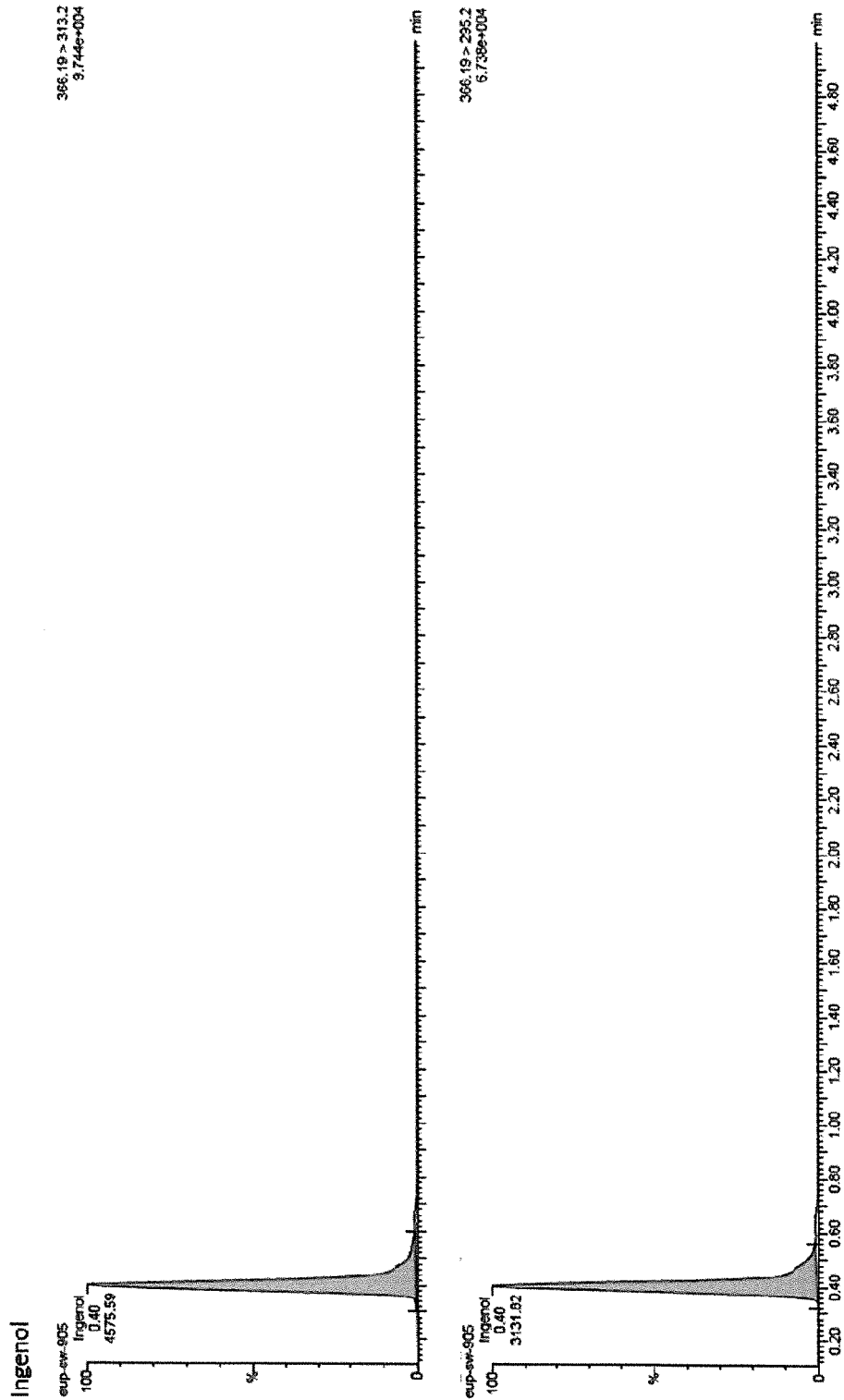

FIG. 7: UPLC-MS/MS-spectra of *Euphorbia peplus* biomass samples derived from non-embryogenic cell suspension culture. Two daughter ions (first graph m/z=295.2 and second graph m/z=313.2) obtained from the mother ion of Ingenol (m/z=366.19; M+NH$_4^+$) were detected above the noise level in samples derived from non-embryogenic *Euphorbia peplus* suspension cell culture.

Figure 8:
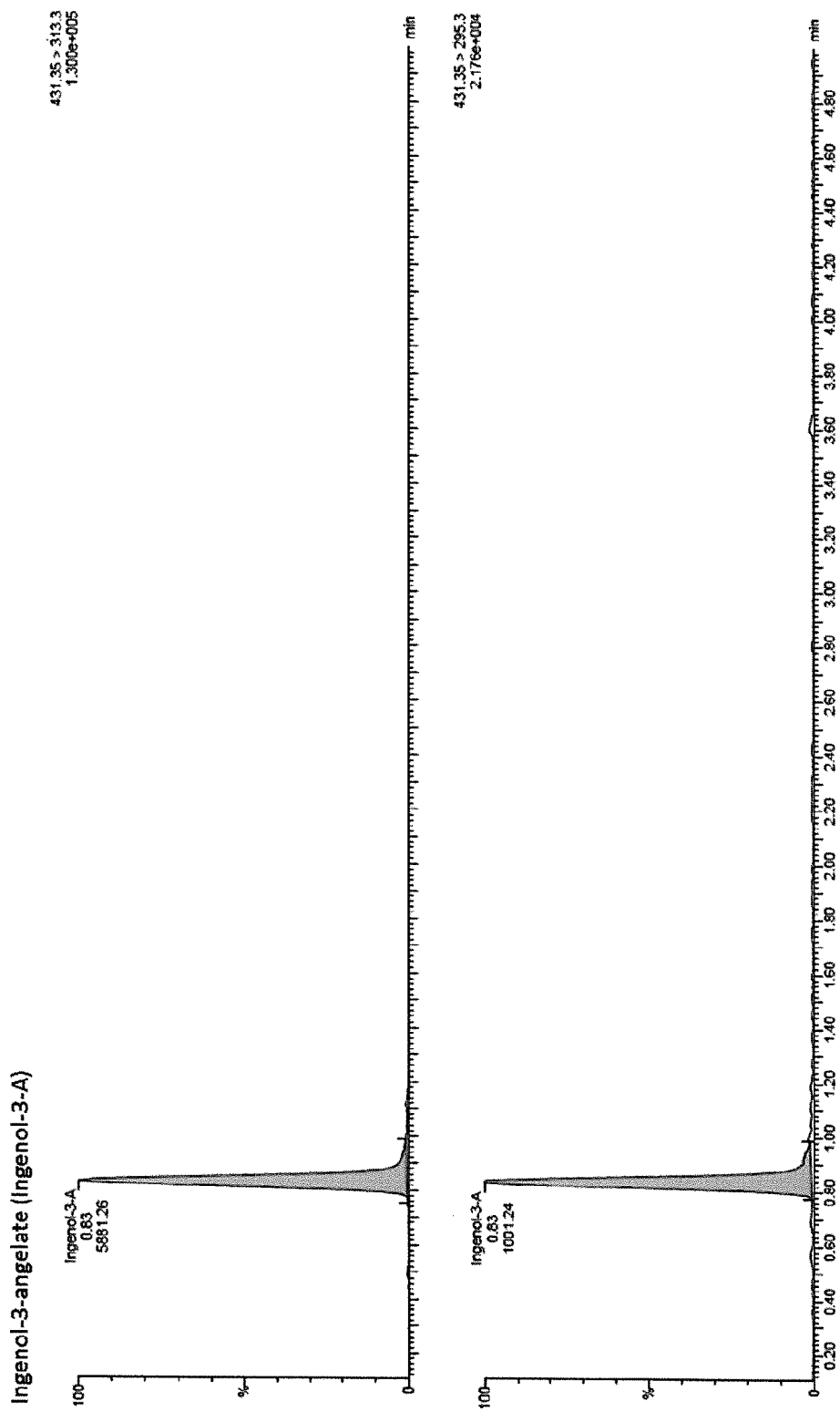

FIG. 8: UPLC-MS/MS-spectra of *Euphorbia peplus* biomass samples derived from non-embryogenic cell suspension culture. Two daughter ions (first graph m/z=295.3 and second graph m/z=313.3) obtained from the mother ion of the Ingenol ester Ingenol-3-angelate (m/z=431.35; M+NH$_4^+$) were detected above the noise level in samples derived from non-embryogenic *Euphorbia peplus* suspension cell culture.

Figure 9:
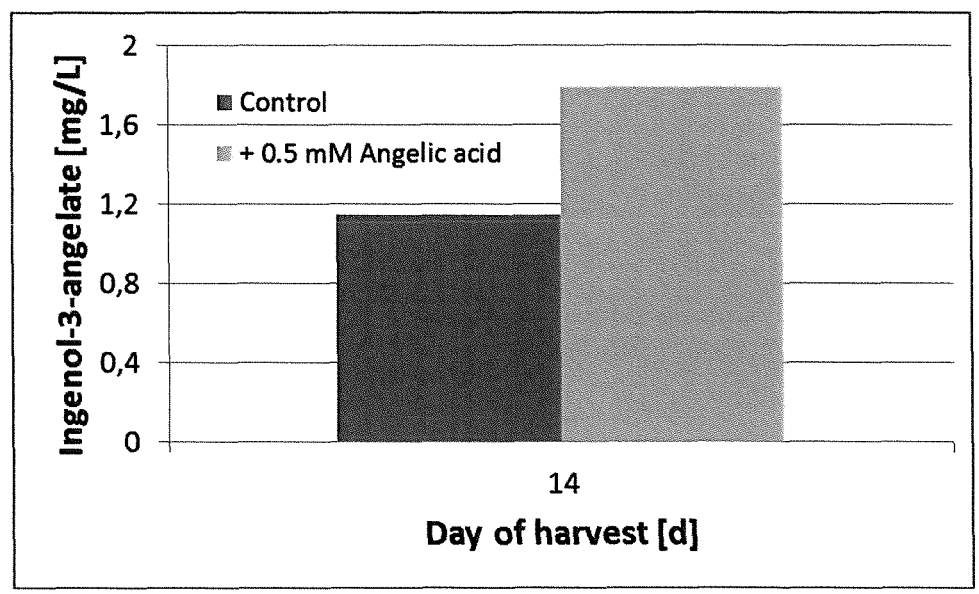

FIG. 9: Concentration of Ingenol-3-angelate recovered from 1 liter suspension culture (comprising the supernatant and 250 g biomass) of *Euphorbia peplus* cultured in MS-medium (full strength basal salt, 2% sucrose, supplemented with 0.5 mg/l BAP and 0.5 mg/l 2,4-D) with and without supplementation with 0.5 mM angelic acid and harvested at day 14. In the absence of angelic acid, a concentration of 1.14 mg Ingenol-3-angelate was detected in 1 liter of suspension culture, corresponding to 4.56 mg Ingenol-3-angelate produced by one kg (fresh biomass) of cells. In the presence of 0.5 mM angelic acid, a concentration of 1.8 mg Ingenol-3-angelate was detected in 1 liter of suspension culture, corresponding to 7.2 mg Ingenol-3-angelate produced by one kg (fresh biomass) of cells.

The examples illustrate the invention:

EXAMPLE 1

Surface Sterilisation of Intact Plant Material

Intact plant material of *Euphorbia peplus* (roots, stems and leaves) was thoroughly washed with tap water. The intact plant material was cut into small pieces (plant explants) of approx. 3-4 cm. Plant explants were washed in detergent and under running water for about 10 to 15 minutes. The explants were surface sterilised by dipping explants in a 70% isopropyl alcohol (IPA) (v/v) solution containing 2-3 drops of Tween 20 for 1 minute (gently agitated during this time). Afterwards, explants were stored in a NaOCl solution (2.8 g/100 ml sodium hypochlorite) for 15 to 30 minutes depending on the part of the plant. Subsequently explants were briefly rinsed with sterile distilled water 3 to 4 times to remove all traces of the sterilising agents. After surface disinfection, the explants were kept in covered Petri dishes in the laminar flow cabinet until ready to process to avoid dehydration. Before the explants were placed on solid culture medium, the cut ends of explants were removed with a sterile scalpel and the explants were cut into smaller pieces of an appropriate size (0.25-0.5 cm).

EXAMPLE 2

Friable Callus Induction on Solid Medium

Plant explants were placed on solid modified basal media of Murashige and Skoog (half strength MS basal salt, 2% sucrose, supplemented with 0.5 mg/l benzylaminopurine (BAP) and 0.5 mg/l 2,4-dichlorophenoxyacetic acid (2,4-D)). Cultures were incubated in darkness in an incubator maintained at 25±2° C. After 4-6 weeks, primary callus material was obtained. The primary callus material was removed from the explant and transferred on fresh solid medium. The frequency of transfer of calli depended on the growth rate and ranged from 4-8 weeks. The plant explants obtained were the *Euphorbia peplus* explants prepared according to example 1.

EXAMPLE 3

Initiation of Suspension Cultures of *E. Peplus*

For the initiation of suspension cultures, friable callus material (approximately 40-60 g/l) was transferred into MS-medium (full strength basal salt, 2% sucrose, supplemented with 0.5 mg/l BAP and 0.5 mg/l 2,4-D). The suspension cultures were cultivated in 250 ml Erlenmeyer flasks in 50 ml cultivation medium on a rotary shaker at 130 rpm in the dark. The cultivation temperature was 25±2° C. Depending on cell growth, suspensions of *E. peplus* were transferred after between 6-14 days by inoculating 40-60 g/l biomass into fresh cultivation medium as described above.

EXAMPLE 4

Maintenance of Suspension Cultures of *E. Peplus*

Maintenance of *E. peplus* suspension cultures was performed weekly by transferring 40-60 g/l vacuum-filtrated biomass in fresh MS-medium (full strength basal salt, 2% sucrose, supplemented with 0.5 mg/l BAP and 0.5 mg/l 2,4-D). The cultures were maintained in 250 ml Erlenmeyer flasks containing 50 ml liquid medium. Finally, cells were cultivated in the dark at 130 rpm at 25±2° C.

EXAMPLE 5

Extraction of Biomass of *E. Peplus*

Biomass of *E. peplus* (either callus material or vacuum-filtrated biomass from suspensions) was quenched with liquid nitrogen directly after sampling to stop metabolic activity. Afterwards, biomass samples were lyophilized. To make an extract, lyophilized biomass samples were weighed out and approx. 15-20 times 80% ethanol and 20% ammonium acetate buffer pH 1.5 was added. The cells were disrupted for 90 sec in a bead mill (2 beads) and this mixture was subsequently centrifuged for 10 min (14.000 rpm) to receive the crude extract which was used for further analysis.

EXAMPLE 6

Extraction of Suspension of *E. Peplus*

A sample of a suspension culture of *E. peplus* was lyophilized and subsequently weighed out. The lyophilisate was resuspended in 15-20 times volume of 80% ethanol and 20% ammonium acetate buffer pH 1.5. This mixture was homogenized for 90 sec in a bead mill (using two beads) and subsequently centrifuged for 10 min (14.000 rpm) to receive the crude extract which was used for further analysis. The lyophilized suspension culture contains both the supernatant and the biomass. Accordingly, the combined concentration of compounds released into the supernatant and compounds present within the cells was measured by this approach. As shown in FIG. 9, a concentration of 1.14 mg Ingenol-3-angelate was detected in 1 liter of suspension culture, corresponding to 4.56 mg Ingenol-3-angelate per kg fresh biomass. In the additional presence of 0.5 mM angelic acid, an even higher concentration of 1.8 mg Ingenol-3-angelate was detected in 1 liter of suspension culture, corresponding to 7.2 mg Ingenol-3-angelate per kg fresh biomass.

EXAMPLE 7

Cryopreservation and Thawing

A 7 day old vacuum-filtrated biomass sample of *E. peplus* was transferred into modified MS-medium (full strength basal salt, 5% sucrose, supplemented with 0.5 mg/l BAP and 0.5 mg/l 2,4-D). After 7 days approx. 0.5 g vacuum-filtrated cells were transferred into 1.5 ml of a 1 M sucrose solution containing 0.5 M dimethyl sulfoxide (DMSO) and 0.5 M glycerol as cryoprotectants and stored for 60 min on ice. Afterwards the vials were cooled in a low temperature freezer (at least −70° C.) to −40° C. by the use of the Nalgene® freezing container Mr. Frosty™ (cooling rate: −1° C. per minute) and afterwards the vials were stored for 8 days in liquid nitrogen.

For the thawing procedure, the vials were dipped into a water bath (45° C.) for approximately 90 sec. The thawed solution was poured into 10 ml washing solution containing 0.25 M sorbitol and 0.0025 M $CaCl_2 \times 2\ H_2O$. After 10 min, the biomass was separated from the solution and plated out on solid MS-medium (half strength MS basal salt, 2% sucrose, supplemented with 0.5 mg/l BAP and 0.5 mg/l 2,4-D). Plates were then incubated in darkness in an incubator maintained at 25±2° C. After 4-6 weeks recovered callus material was obtained. The experiments described herein for freshly prepared cells were repeated with these cryopreserved and thawed cells and the ability of the thawed cells to produce the compounds of interest in accordance with the present invention was confirmed.

EXAMPLE 8

Ingenol and Ingenol-3-angelate Expression in Suspension Culture

Suspension cultures were inoculated with about 50 g biomass (fresh weight)/l and cultivated in MS-medium (full strength basal salts, 2% sucrose, supplemented with 0.5 mg/l BAP and 0.5 mg/l 2,4-D). The suspension cultures were cultivated in 250 ml Erlenmeyer flasks in 50 ml cultivation medium on a rotary shaker at 130 rpm in the dark. The cultivation temperature was 25±2° C. *Euphorbia peplus* biomass was harvested on days 7 and 14 and Ingenol concentration (see FIG. 1) and Ingenol-3-angelate concentration (see FIG. 2) were determined after recovery.

EXAMPLE 9

Precursor Feeding with Angelic Acid

Further increase of Ingenol-3-angelate was achieved using angelic acid as a precursor. A suspension culture of *E. peplus*, newly transferred or up to 14 days old, was supplemented with 0.5 mM angelic acid. After addition, no influence on cell growth was observed. The same amount of sterile water was used as a negative control. After addition of angelic acid, the culture was cultivated for 7-14 days (see FIG. 6).

EXAMPLE 10

Induction of Ingenol and Ingenol-3-angelate with Salicylic Acid

To induce Ingenol and Ingenol-3-angelate expression, salicylic acid was used as elicitor. A 7 day suspension culture of *E. peplus* (50 ml) was supplemented with 30 μM salicylic acid. For the respective negative controls, the same amount of sterile water was used. After induction, the culture was further cultivated for 9 days resulting in total cultivation time to harvest of 16 days (Ingenol: see FIG. 3 and Ingenol-3-angelate: see FIG. 4).

EXAMPLE 11

Induction of Ingenol-3-angelate with Methyl Jasmonate

To induce Ingenol-3-angelate expression, methyl jasmonate was used as elicitor. A 7 day suspension culture of *E. peplus* (50 ml) was supplemented with 1 μM methyl jasmonate. For the respective negative controls, the same amount of sterile water was used. After induction, the culture was further cultivated for 9 days resulting in total cultivation time to harvest of 16 days (see FIG. 5).

EXAMPLE 12

Analysis of Ingenols—Ingenol

The following method was used for the detection Ingenol:

| | |
|---|---|
| Column: | C18, Waters Acquity UPLC BEH C18, 2.1 × 50 mm; 1.7μ |
| Chromatograph: | UPLC, Waters Acquity UPLC, with binary pump |
| Solvent: | A: 10 mmol Ammonium acetate buffer + 0.1% Formic acid |
| | B: Acetonitrile + 0.1% Formic acid |

| | Time (min): | 0.00 | 1.50 | 2.00 | 3.00 | 3.10 | 5.00 |
|---|---|---|---|---|---|---|---|
| Gradient: | % solvent A: | 34 | 34 | 0 | 0 | 34 | 34 |
| | % solvent B: | 66 | 66 | 100 | 100 | 66 | 66 |

| | |
|---|---|
| Run time: | 5.00 min |
| Flow: | 0.4 ml/min |
| Injection volume: | 4 μl |
| Retention time: | approximately 0.40 min (Ingenol) |
| Detector: | Mass spectrometer, Waters Quattro Premier |
| Detection: | ESI+ |
| Identification Conditions: | Ingenol m/z = 366.19 -> 295.2/366.19 -> 313.2 |
| | Capillary Voltage: 1.0 kV |
| | Cone Voltage: 15 V |
| | Source Temp: 150° C. |
| | Desolvation Temp: 400° C. |
| | Desolvation Gas: 800 l/h |
| | Cone Gas: 50 l/h |

Applying these conditions to cell extracts described e.g. in example 6, Ingenol was clearly identified in the sample (see FIG. 7) by comparison to a reference material.

EXAMPLE 13

Analysis of Ingenols—Ingenol-3-angelate

The following method was used for the detection of Ingenol-3-angelate:

| Column: | C18, Waters Acquity UPLC BEH C18, 2.1 × 50 mm; 1.7μ |
| --- | --- |
| Chromatograph: | UPLC, Waters Acquity UPLC, with binary pump |
| Solvent: | A: 10 mmol Ammonium acetate buffer + 0.1% Formic acid |
| | B: Acetonitrile + 0.1% Formic acid |

| | Time (min): | 0.00 | 1.50 | 2.00 | 3.00 | 3.10 | 5.00 |
| --- | --- | --- | --- | --- | --- | --- | --- |
| Gradient: | % solvent A: | 34 | 34 | 0 | 0 | 34 | 34 |
| | % solvent B: | 66 | 66 | 100 | 100 | 66 | 66 |

| Run time: | 5.00 min |
| --- | --- |
| Flow: | 0.4 ml/min |
| Injection volume: | 4 μl |
| Retention time: | approximately 0.88 min (Ingenol-3-angelate) |
| Detector: | Mass spectrometer, Waters Quattro Premier |
| Detection: | ESI+ |
| Identification Conditions: | Ingenol-3-angelate m/z = 431.35 -> 295.3/ 431.35 -> 313.3 |
| | Capillary Voltage: 1.0 kV |
| | Cone Voltage: 15 V |
| | Source Temp: 150° C. |
| | Desolvation Temp: 400° C. |
| | Desolvation Gas: 800 l/h |
| | Cone Gas: 50 l/h |

Applying these conditions to cell extracts described e.g. in example 6, Ingenol-3-angelate was clearly identified in the sample (see FIG. 8) by comparison to a reference material.

EXAMPLE 14

Materials

The following materials were obtained from the following suppliers:

| Material | Supplier |
| --- | --- |
| MS-Medium | PhytoTechnology Laboratories |
| Methyl jasmonate | Bedoukian |
| Salicylic acid | Sigma Aldrich |
| Angelic acid | TCI GmbH |
| Benzylaminopurine | Sigma Aldrich |
| Dichlorophenoxyacetic acid | Duchefa Biochemie |
| Sucrose | Riedel-de Haën |
| Strata-X (1 ml) | Phenomenex |
| Ammonium acetate | Fluka |
| Ethanol | Merck |
| Sodium hypochlorite | Merck |
| Isopropyl alcohol | Merck |
| Tween 20 | Sigma Aldrich |
| Gelrite ® | Duchefa Biochemie |
| Dimethyl sulfoxide | Sigma Aldrich |
| Glycerol | Sigma Aldrich |
| Liquid nitrogen | Air Liquide |
| Sorbitol | Sigma Aldrich |
| Calcium chloride | Merck |
| SEFAR Nitex 90 μM | Sefar AG |
| Sepabeads ® SP-207 | Resindion S.R.L. |
| Amberlite XAD | Sigma Aldrich |
| Diaion HP-20 | Sigma Aldrich |
| Glacial acetic acid | Th. Geyer GmbH & Co. KG |
| Acetone | Th. Geyer GmbH & Co. KG |

EXAMPLE 15

Extraction of Supernatant of E. Peplus

Supernatant was separated from biomass via vacuum filtration and subsequently lyophilized. The lyophilized samples were resuspended in 15-20 times volume of 80% ethanol and 20% ammonium acetate buffer pH 1.5. This mixture was homogenized for 90 sec in a bead mill (using two beads) and subsequently centrifuged for 10 min (14.000 rpm) to receive the crude extract which was used for further analysis. The presence of Ingenol-3-angelate and Ingenol in the supernatant was confirmed and the respective concentrations determined in repeated experiments.

EXAMPLE 16

Recovery of Ingenol from E. Peplus Suspension Cultures by Resin Adsorption

Recovery of Ingenol from *Euphorbia peplus* cell suspension cultures producing Ingenol was achieved by the use of adsorbent resins. In order to recover Ingenol 2 ml sterile resin (e.g. Sepabeads SP207 or Amberlite XAD1180N or Diaion HP-20), 3 ml Ethanol and 150 μl of Acetic acid were added to 30 ml of a 14-day old suspension culture of *E. peplus* grown under growth conditions. To simplify separation of the resin, it was embedded in a SEFAR tissue bag. Harvesting of the resin bags after 5 h, 24 h, 48 h and 120 h of shaking in the suspension at room temperature was tested and it was confirmed that at all times Ingenol could be recovered, with highest amounts being obtained after 120 h of shaking. Subsequently, the resin bags were separated from the cell suspension broth and were washed thrice thoroughly with deionized water. In one example two ml of resin (1 bed volume, BV) was desorbed with 8-10 ml (4-5 BV) of organic solvent like e.g. Acetone or alcohol, with and without additional acidification. In one example the resin was desorbed with 10 ml pure ethanol acidified with 500 μl glacial acetic acid for 30 min. The recovered Ingenol content in the supernatant after separation from the resin was detected and quantified with LC/MS as described above.

EXAMPLE 17

Recovery of Ingenol-3-angelate from E. Peplus Suspension Cultures by Resin Adsorption Recovery of Ingenol-3-angelate from *Euphorbia peplus* cell suspension cultures producing Ingenol-3-angelate was achieved by the use of adsorbent resins. In order to recover Ingenol-3-angelate, 2 ml sterile resin (e.g. Sepabeads SP207 or Amberlite XAD1180N or Diaion HP-20), 3 ml Ethanol and 150 μl of Acetic acid were added to 30 ml of a 14-day old suspension culture of *E. peplus* grown under growth conditions. To simplify separation of the resin, it was embedded in a SEFAR tissue bag. Harvesting of the resin bags after 5 h, 24 h, 48 h and 120 h of shaking in the suspension at room temperature was tested and it was confirmed that at all times Ingenol-3-angelate could be recovered, with highest amounts being obtained after 120 h of shaking. Subsequently, the resin bags were separated from the broth and were washed thrice thoroughly with deionized water. In one example two ml of resin (1 bed volume, BV) was desorbed with 8-10 ml (4-5 BV) of organic solvent like e.g. Acetone or alcohol, with and without additional acidification. In one example the resin was desorbed with 10 ml pure ethanol acidified with 500 μl glacial acetic acid for 30 min. The recovered Ingenol-3-angelate content in the supernatant after separation from the resin was detected and quantified with LC/MS as described above.

EXAMPLE 18

In Situ Recovery of Ingenol from *E. Peplus* Suspension Cultures by Resin Adsorption For the in situ recovery of Ingenol an adsorbent resin was used. Fresh MS-medium (full strength basal salt, 2% sucrose, supplemented with 0.5 mg/l BAP and 0.5 mg/l 2,4-D) was inoculated with 40-60 g/L vacuum-filtrated biomass of *E. peplus*. The cultures were cultivated in 250 ml Erlenmeyer flasks containing 50 ml liquid medium. Two ml of a sterile resin (e.g. Sepabeads SP207 or Amberlite XAD1180N or Diaion HP-20), embedded in a SEFAR tissue bag, was added directly to the inoculated culture. In the presence of the resin containing SEFAR tissue bag, the viable cell suspension culture was cultivated in the dark at 130 rpm for 14 days at 25° C.±2° C. Afterwards the resin bag was separated from the cell suspension broth and was washed thrice thoroughly with deionized water. In one example two ml of resin (1 bed volume, BV) was desorbed with 8-10 ml (4-5 BV) of organic solvent like e.g. Acetone or alcohol, with and without additional acidification. In one example the resin was desorbed with 10 ml pure ethanol acidified with 500 µl glacial acetic acid for 30 min. The recovered Ingenol content in the supernatant after separation from the resin was detected and quantified with LC/MS as described above.

EXAMPLE 19

In Situ Recovery of Ingenol-3-angelate From *E. Peplus* Suspension Cultures by Resin Adsorption For the in situ recovery of Ingenol-3-angelate an adsorbent resin was used. Fresh MS-medium (full strength basal salt, 2% sucrose, supplemented with 0.5 mg/l BAP and 0.5 mg/l 2,4-D) was inoculated with 40-60 g/L vacuum-filtrated biomass of *E. peplus*. The cultures were cultivated in 250 ml Erlenmeyer flasks containing 50 ml liquid medium. Two ml of a sterile resin (e.g. Sepabeads SP207 or Amberlite XAD1180N or Diaion HP-20), embedded in a SEFAR tissue bag, was added directly to the fresh inoculated culture. In the presence of the resin containing SEFAR tissue bag the viable cell suspension culture was cultivated in the dark at 130 rpm for 14 days at 25° C.±2° C. Afterwards the resin bag was separated from the cell suspension broth and was washed thrice thoroughly with deionized water. In one example two ml of resin (1 bed volume, BV) was desorbed with 8-10 ml (4-5 BV) of organic solvent like e.g. Acetone or alcohol, with and without additional acidification. In one example the resin was desorbed with 10 ml pure ethanol acidified with 500 µl glacial acetic acid for 30 min. The recovered Ingenol-3-angelate content in the supernatant after separation from the resin was detected and quantified with LC/MS as described above.

EXAMPLE 20

Surface Sterilization of *Euphorbia Lathyris* Seeds

Seeds of *Euphorbia lathyris* were thoroughly washed with tap water. Seeds were washed in detergent and under running water for about 10 to 15 minutes. The explants were surface sterilized by dipping seeds in a 70% isopropyl alcohol (IPA) (v/v) solution containing 2-3 drops of Tween 20 for 1 minute (gently agitated during this time). Afterwards, seeds were stored in a NaOCl solution (2.8 g/100 ml sodium hypochlorite) for 30 minutes. Subsequently seeds were briefly rinsed with sterile distilled water 3 to 4 times to remove all traces of the sterilizing agents. After surface disinfection the seeds were kept in covered Petri dishes in the laminar flow cabinet until ready to process to avoid dehydration. Seeds were then placed on solid medium for callus generation.

EXAMPLE 21

Friable Callus Induction of *Euphorbia Lathyris* on Solid Medium

Sterile seeds were cut and placed on solid modified basal media of Murashige and Skoog (half strength MS basal salt, 2% sucrose, supplemented with 0.5 mg/l BAP and 0.5 mg/l 2,4-D). Cultures were then incubated in darkness in an incubator maintained at 25±2° C. After 4-6 weeks primary callus material was obtained. The primary callus material was removed from the seed and transferred on fresh solid medium. The frequency of transferring of calli depended on the growth rate and ranged from 4-8 weeks.

EXAMPLE 22

Initiation of Suspension Cultures of *E. Lathyris*

For the initiation of suspension cultures friable callus material (approximately 40-60 g/l) was transferred into MS-medium (full strength basal salt, 2% sucrose, supplemented with 0.5 mg/l BAP and 0.5 mg/l 2,4-D). The suspension cultures grew in larger cell aggregates and were cultivated in 250 ml Erlenmeyer flasks in 50 ml cultivation medium on a rotary shaker at 130 rpm in the dark. The cultivation temperature was 25±2° C. Depending on cell growth suspensions of *E. lathyris* were transferred in a range of 6-14 days by inoculating 40-60 g/l biomass into fresh cultivation medium as described above.

EXAMPLE 23

Maintenance of Suspension Cultures of *E. Lathyris*

Maintenance of *E. lathyris* suspension cultures was performed weekly by transferring 40-60 g/l vacuum-filtrated biomass in fresh MS-medium (full strength basal salt, 2% sucrose, supplemented with 0.5 mg/l BAP and 0.5 mg/l 2,4-D). The cultures were maintained in 250 ml Erlenmeyer flasks containing 50 ml liquid medium. Finally, cells were cultivated in the dark at 130 rpm at 25±2° C.

EXAMPLE 24

Extraction of Biomass of *E. Lathyris*

Biomass of *E. lathyris* (either callus material or vacuum-filtrated biomass from suspensions) was quenched with liquid nitrogen directly after sampling to stop metabolic activity. Afterwards, biomass samples were lyophilized. To make an extract, lyophilized biomass samples were weighed out and approx. 15-20 times 80% ethanol and 20% ammonium acetate buffer pH 1.5 was added. The cells were disrupted for 90 sec in a bead mill (2 beads) and this mixture was subsequently centrifuged for 10 min (14.000 rpm) to receive the crude extract which was used for further analysis.

EXAMPLE 25

Extraction of Supernatant of *E. Lathyris*

Supernatant is separated via vacuum filtration from the biomass and lyophilized. The lyophilisate was resuspended in 15-20 times volume of as 80% ethanol and 20% ammonium acetate buffer pH 1.5. This mixture was homogenized for 90 sec in a bead mill (using two beads) and subsequently centrifuged for 10 min (14.000 rpm) to receive the crude extract which was used for further analysis.

Extraction of suspensions can also be carried out by following the procedure described in Example 6 above.

The presence of ingenol-3-angelate and ingenol was confirmed in various samples and the respective concentrations determined in repeat experiments.

EXAMPLE 26

Surface Sterilization of *Euphorbia Epithymoides* Seeds

Seeds of *Euphorbia epithymoides* were thoroughly washed with tap water. Seeds were washed in detergent and under running water for about 10 to 15 minutes. The explants were surface sterilized by dipping seeds in a 70% isopropyl alcohol (IPA) (v/v) solution containing 2-3 drops of Tween 20 for 1 minute (gently agitated during this time). Afterwards, seeds were stored in a NaOCl solution (2.8 g/100 ml sodium hypochlorite) for 30 minutes. Subsequently seeds were briefly rinsed with sterile distilled water 3 to 4 times to remove all traces of the sterilizing agents. After surface disinfection the seeds were kept in covered Petri dishes in the laminar flow cabinet until ready to process to avoid dehydration. Seeds were then placed on solid medium for callus generation.

EXAMPLE 27

Friable Callus Induction of *Euphorbia Epithymoides* on Solid Medium

Sterile seeds were cut and placed on solid modified basal media of Murashige and Skoog (half strength MS basal salt, 2% sucrose, supplemented with 0.5 mg/l BAP and 0.5 mg/l 2,4-D). Cultures are then incubated in darkness in an incubator maintained at $25\pm2°$ C. After 4-6 weeks primary callus material was obtained. The primary callus material was removed from the seed and transferred on fresh solid medium. The frequency of transfer of calli depended on the growth rate and ranged from 4-8 weeks.

EXAMPLE 28

Initiation of Suspension Cultures of *Euphorbia Epithymoides*

For the initiation of suspension cultures friable callus material (approximately 40-60 g/l) was transferred into MS-medium (full strength basal salt, 2% sucrose, supplemented with 0.5 mg/l BAP and 0.5 mg/l 2,4-D). The suspension cultures were cultivated in 250 ml Erlenmeyer flasks in 50 ml cultivation medium on a rotary shaker at 130 rpm in the dark. The cultivation temperature was $25\pm2°$ C. Depending on cell growth suspensions of *Euphorbia epithymoides* were transferred in a range of 6-14 days by inoculating 40-60 g/l biomass into fresh cultivation medium as described above.

EXAMPLE 29

Maintenance of Suspension Cultures of *Euphorbia Epithymoides*

Maintenance of *Euphorbia epithymoides* suspension cultures was performed weekly by transferring 40-60 g/l vacuum-filtrated biomass in fresh MS-medium (full strength basal salt, 2% sucrose, supplemented with 0.5 mg/l BAP and 0.5 mg/l 2,4-D). The cultures were maintained in 250 ml Erlenmeyer flasks containing 50 ml liquid medium. Finally, cells were cultivated in the dark at 130 rpm at $25\pm2°$ C.

EXAMPLE 30

Cryopreservation and Thawing of *Euphorbia Epithymoides*

A 7 day old vacuum-filtrated biomass sample of *Euphorbia epithymoides* was transferred into modified MS-medium (full strength basal salt, 5% sucrose, supplemented with 0.5 mg/l BAP and 0.5 mg/l 2,4-D). After 7 days approx. 0.5 g vacuum-filtrated cells were transferred into 1.5 ml of a 1 M sucrose solution containing 0.5 M dimethyl sulfoxide (DMSO) and 0.5 M glycerol as cryoprotectants and stored for 60 min on ice. Afterwards the vials were cooled in a low temperature freezer (at least $-70°$ C.) to $-40°$ C. by the use of the Nalgene® freezing container Mr. Frosty™ (cooling rate: $-1°$ C. per minute) and afterwards the vials were stored for 8 days in liquid nitrogen.

For the thawing procedure, the vials were dipped into a water bath ($45°$ C.) for approximately 90 sec. The thawed solution was poured into 10 ml washing solution containing 0.25 M sorbitol and 0.0025 M $CaCl_2 \times 2\ H_2O$. After 10 min, the biomass was separated from the solution and plated out on solid MS-medium (half strength MS basal salt, 2% sucrose, supplemented with 0.5 mg/l BAP and 0.5 mg/l 2,4-D). Plates were then incubated in darkness in an incubator maintained at $25\pm2°$ C. After 4-6 weeks recovered callus material was obtained. Callus material can be used for initiation of suspension cell cultures and subsequently production and recovery of Ingenol and/or Ingenol-3-angelate can be achieved as described previously.

EXAMPLE 31

Extraction of Biomass of *Euphorbia Epithymoides*

Biomass of *Euphorbia epithymoides* (either callus material or vacuum-filtrated biomass from suspensions) is quenched with liquid nitrogen directly after sampling to stop metabolic activity. Afterwards, biomass samples are lyophilized. To make an extract, lyophilized biomass samples is weighed out and approx. 15-20 times 80% ethanol and 20% ammonium acetate buffer pH 1.5 is added. The cells are disrupted for 90 sec in a bead mill (2 beads) and this mixture is subsequently centrifuged for 10 min (14.000 rpm) to receive the crude extract which is used for further analysis.

EXAMPLE 32

Extraction of Supernatant of *Euphorbia Epithymoides*

Supernatant is separated via vacuum filtration from the biomass and lyophilized. The lyophilisate is resuspended in 15-20 times volume of as 80% ethanol and 20% ammonium acetate buffer pH 1.5. This mixture is homogenized for 90 sec in a bead mill (using two beads) and subsequently centrifuged for 10 min (14.000 rpm) to receive the crude extract which is used for further analysis.

Extraction of suspensions can also be carried out by following the procedure described in Example 6 above.

EXAMPLE 33

Analysis of Ingenol Esters

The following method was used for the detection of Ingenol-3-mebutate:

| | |
|---|---|
| Column: | C18, like e.g. Phenomenex Synergi 4 μm Hydro-RP 80A, 4.6 × 250 mm |
| Chromatograph: | HPLC, like e.g. Agilent 1200 Series, with binary pump |
| Solvent: | A: deionized Water |
| | B: Acetonitrile |
| Solvent mixture: | % solvent A: 34 |
| | % solvent B: 66 |
| Run time: | 6.00 min |
| Flow: | 2 ml/min |
| Injection volume: | 20 μl |
| Retention time: | Ingenol-5-angelate → approximately 3.29 min |
| | Ingenol-20-angelate → approximately 4.42 min |
| | Ingenol-3-tiglate → approximately 4.67 min |
| | Ingenol-3-angelate → approximately 5.26 min |
| Detector: | Diode array detector, like e.g. Agilent DAD 1200 Series |
| Wavelength: | 225 nm |

The application of these conditions to cell extracts described allows the detection of Ingenol esters. Whereas the above listed Ingenol esters Ingenol-5-angelate, Ingenol-20-angelate and Ingenol-3-tiglate were identified in plant cell culture derived cell extracts by its retention times, Ingenol-3-angelate was further characterized and identified by comparison to a reference material.

The invention claimed is:

1. A method of producing Ingenol, Ingenol esters and/or Tiglian-3-one derivatives, the method comprising the steps of:
    (a) culturing plant cells obtained from a plant selected from the family Euphorbiaceae in a nutrient medium in a suspension cell culture, wherein the cells produce Ingenol, one or more Ingenol esters and/or one or more Tiglian-3-one derivatives; and
    (b) recovering the Ingenol, the one or more Ingenol esters and/or the one or more Tiglian-3-one derivatives produced in (a).

2. The method of claim 1, further comprising prior to step (a) an additional step of:
    (a-0) culturing explants of a plant from the family Euphorbiaceae on medium, thereby obtaining friable callus material.

3. The method according to claim 1, wherein the nutrient medium in step (a) is supplemented with one or more chemical compounds inducing the biosynthetic pathway to Ingenol and/or Ingenol esters and/or Tiglian-3-one derivatives.

4. The method according to claim 1, wherein the plant selected from the family Euphorbiaceae is of the genus *Euphorbia*, preferably of the species *Euphorbia peplus*, *Euphorbia lathyris*, or *Euphorbia epithymoides*.

5. The method according to claim 4, wherein Ingenol and/or one or more Ingenol esters are recovered in (b).

6. The method according to claim 5, wherein the compound recovered in step (b) is Ingenol-3-angelate and wherein the nutrient medium in step (a) is supplemented with angelic acid.

7. The method according to claim 1, wherein the plant selected from the family Euphorbiaceae is of the genus *Fontainea* or *Hylandia*, preferably of a species selected from the group consisting of *Fontainea picrosperma*, *Fontainea venosa* and *Hylandia dockrillii*.

8. The method according to claim 7, wherein one or more Tiglian-3-one derivatives are recovered in (b).

9. A plant suspension cell culture, wherein the cells are cells obtained from a plant selected from the family Euphorbiaceae, wherein the plant cells produce Ingenol and/or one or more Ingenol esters and/or one or more Tiglian-3-one derivatives.

10. A plant cell biomass comprising plant cells obtained from the suspension cell culture according to claim 9, and comprising Ingenol and/or one or more Ingenol esters and/or one or more Tiglian-3-one derivatives.

11. Cryopreserved cell(s) of a plant suspension cell culture according to claim 9.

12. The method of claim 1, wherein the plant cells for culture in step (a) are obtained from the cryopreserved cells according to claim 11.

* * * * *